US012605563B2

(12) United States Patent
Marsteller et al.

(10) Patent No.: US 12,605,563 B2
(45) Date of Patent: Apr. 21, 2026

(54) SYSTEM FOR BRACHYTHERAPY

(71) Applicant: RADIANCE THERAPEUTICS, INC.,
Tucson, AZ (US)

(72) Inventors: Laurence J. Marsteller, Tucson, AZ
(US); James A. Fazio, Tucson, AZ
(US); Michael Williams, Carlsbad, CA
(US); Audrey Cohen, Tucson, AZ
(US); Bob Eisele, Carlsbad, CA (US);
Zachary Engelder, Carlsbad, CA (US)

(73) Assignee: RADIANCE THERAPEUTICS, INC.,
Tucson, AZ (US)

( * ) Notice: Subject to any disclaimer, the term of this
patent is extended or adjusted under 35
U.S.C. 154(b) by 1097 days.

(21) Appl. No.: 17/676,711

(22) Filed: Feb. 21, 2022

(65) Prior Publication Data

US 2022/0176154 A1      Jun. 9, 2022

Related U.S. Application Data

(63) Continuation-in-part of application No.
PCT/US2020/047235, filed on Aug. 20, 2020, and a
(Continued)

(30) Foreign Application Priority Data

Sep. 7, 2017      (GB) ...................................... 1714392

(51) Int. Cl.
A61N 5/10              (2006.01)
(52) U.S. Cl.
CPC ...... A61N 5/1028 (2013.01); A61N 2005/109
(2013.01)

(58) Field of Classification Search
CPC .. A61N 5/1001; A61N 5/1002; A61N 5/1007;
A61N 5/1014–1017;
(Continued)

(56) References Cited

U.S. PATENT DOCUMENTS

| 1,525,158 | A | 2/1925 | Viol |
| 1,733,159 | A | 10/1929 | Each |

(Continued)

FOREIGN PATENT DOCUMENTS

| CA | 643082 A | 6/1962 |
| CN | 107995993 A | 5/2018 |

(Continued)

OTHER PUBLICATIONS

Ayyala et. al., "Comparison of Different Biomaterials for Glaucoma
Drainage Devices." Arch Ophthalmol v. 117 (1999): 233-236, 4
pages.
(Continued)

*Primary Examiner* — Carrie R Dorna
(74) *Attorney, Agent, or Firm* — NGUYEN TARBET IP
LAW

(57) ABSTRACT

Single-use brachytherapy systems for application of beta
radiation to a target tissue, and methods of use. The single-
use brachytherapy systems herein feature a cap into which a
radionuclide brachytherapy source (RBS) can be inserted
and a handle that removably attaches to the cap. When the
handle is disengaged from the cap in order to access the
RBS, the system is rendered useless for its original purpose,
for its use as it was originally intended, for its use as
prescribed, unless repaired.

7 Claims, 15 Drawing Sheets

Related U.S. Application Data continuation-in-part of application No. PCT/US2021/064141, filed on Dec. 17, 2021, which is a continuation-in-part of application No. PCT/US2021/012694, filed on Jan. 8, 2021, and a continuation-in-part of application No. PCT/US2021/012744, filed on Jan. 8, 2021, application No. 17/676,711 is a continuation-in-part of application No. PCT/US2021/064190, filed on Dec. 17, 2021, which is a continuation-in-part of application No. PCT/US2021/012694, filed on Jan. 8, 2021, and a continuation-in-part of application No. PCT/US2021/012744, filed on Jan. 8, 2021, application No. 17/676,711 is a continuation-in-part of application No. PCT/US2020/063435, filed on Dec. 4, 2020, and a continuation-in-part of application No. PCT/US2021/012744, filed on Jan. 8, 2021, and a continuation-in-part of application No. PCT/US2021/012694, filed on Jan. 8, 2021, and a continuation-in-part of application No. 16/698,676, filed on Nov. 27, 2019, now Pat. No. 11,273,325, and a continuation-in-part of application No. 16/584,737, filed on Sep. 26, 2019, now Pat. No. 11,666,780, which is a continuation-in-part of application No. PCT/US2018/049400, filed on Sep. 4, 2018, application No. 17/676,711 is a continuation-in-part of application No. 16/810,204, filed on Mar. 5, 2020, now Pat. No. 11,628,310, which is a continuation-in-part of application No. PCT/US2018/049400, filed on Sep. 4, 2018.

(60) Provisional application No. 62/889,461, filed on Aug. 20, 2019, provisional application No. 63/126,855, filed on Dec. 17, 2020, provisional application No. 62/944,952, filed on Dec. 6, 2019, provisional application No. 62/958,554, filed on Jan. 8, 2020, provisional application No. 62/958,517, filed on Jan. 8, 2020, provisional application No. 62/958,634, filed on Jan. 8, 2020, provisional application No. 62/772,741, filed on Nov. 29, 2018, provisional application No. 62/738,573, filed on Sep. 28, 2018.

(58) Field of Classification Search
CPC ................ A61N 5/1027; A61N 5/1028; A61N 2005/1003–1005; A61N 2005/1018; A61N 2005/1019
See application file for complete search history.

(56) References Cited

U.S. PATENT DOCUMENTS

| | | | |
|---|---|---|---|
| 2,517,568 | A | 8/1950 | Hissong |
| 2,559,793 | A | 7/1951 | Pregel |
| D328,644 | S | 8/1992 | Pericic |
| 5,637,073 | A | 6/1997 | Freire |
| D387,162 | S | 12/1997 | Zeimer |
| 6,050,970 | A | 4/2000 | Baerveldt |
| D441,447 | S | 5/2001 | Hjertman et al. |
| 6,274,614 | B1 | 8/2001 | Richter et al. |
| 6,443,881 | B1 | 9/2002 | Finger |
| 6,875,165 | B2 | 4/2005 | Dejuan, Jr. et al. |
| 7,070,554 | B2 | 7/2006 | White et al. |
| D526,411 | S | 8/2006 | Easley |
| 7,109,505 | B1 | 9/2006 | Sliski et al. |
| D621,508 | S | 8/2010 | Bindra |
| D642,266 | S | 7/2011 | Marsteller et al. |
| 8,430,804 | B2 | 4/2013 | Brigatti et al. |
| D691,270 | S | 10/2013 | Marsteller et al. |
| 8,602,959 | B1 | 12/2013 | Park et al. |
| 8,608,632 | B1 | 12/2013 | Brigatti et al. |
| D702,346 | S | 4/2014 | Ben Nun |
| D731,058 | S | 6/2015 | Dietrich |
| D731,060 | S | 6/2015 | Little, III |
| 9,056,201 | B1 | 6/2015 | Hamilton et al. |
| D747,806 | S | 1/2016 | Wargner et al. |
| D748,256 | S | 1/2016 | Wagner et al. |
| D752,749 | S | 3/2016 | Van Dalen et al. |
| D754,331 | S | 4/2016 | Wargner et al. |
| D755,970 | S | 5/2016 | Bergmanson |
| D756,515 | S | 5/2016 | Chin et al. |
| D781,420 | S | 3/2017 | Korenfeld et al. |
| D795,427 | S | 8/2017 | Korenfeld et al. |
| D814,637 | S | 4/2018 | Lohrenz et al. |
| 10,022,558 | B1 | 7/2018 | Marsteller et al. |
| D841,164 | S | 2/2019 | Flowers et al. |
| 10,245,178 | B1 | 4/2019 | Heitzmann et al. |
| 10,576,299 | B1 | 3/2020 | Munro et al. |
| D933,225 | S | 10/2021 | Marsteller et al. |
| D933,226 | S | 10/2021 | Marsteller et al. |
| D939,706 | S | 12/2021 | Van Manen |
| D940,865 | S | 1/2022 | Khan et al. |
| D972,138 | S | 12/2022 | Holderby et al. |
| 2002/0115902 | A1 | 8/2002 | Dejuan, Jr. et al. |
| 2003/0199883 | A1 | 10/2003 | Laks |
| 2004/0138515 | A1 | 7/2004 | White |
| 2005/0277802 | A1 | 12/2005 | Larsen et al. |
| 2006/0111605 | A1 | 5/2006 | Larsen et al. |
| 2006/0212040 | A1 | 9/2006 | Goldstein |
| 2007/0118010 | A1 | 5/2007 | Hillstead et al. |
| 2007/0265485 | A1 | 11/2007 | DeJuan, Jr. et al. |
| 2008/0300444 | A1 | 12/2008 | Ye et al. |
| 2009/0124955 | A1 | 5/2009 | Ayyala |
| 2009/0216062 | A1 | 8/2009 | Axelrod et al. |
| 2010/0000449 | A1 | 1/2010 | Brigatti et al. |
| 2010/0004581 | A1 | 1/2010 | Brigatti et al. |
| 2011/0004045 | A1 | 1/2011 | Larsen et al. |
| 2011/0207987 | A1 | 8/2011 | DiCarlo et al. |
| 2012/0330088 | A1 | 12/2012 | Hillstead et al. |
| 2013/0006033 | A1 | 1/2013 | Cipriani et al. |
| 2013/0211178 | A1 | 8/2013 | Luca et al. |
| 2015/0105601 | A1 | 4/2015 | Finger et al. |
| 2015/0105602 | A1 | 4/2015 | Finger et al. |
| 2015/0105605 | A1 | 4/2015 | Finger et al. |
| 2015/0265850 | A1 | 9/2015 | Finger et al. |
| 2016/0151643 | A1* | 6/2016 | Röder .................. A61N 5/1014 600/1 |
| 2016/0375267 | A1 | 12/2016 | Lutz et al. |
| 2017/0112520 | A1 | 4/2017 | Lavi et al. |
| 2017/0182063 | A1 | 6/2017 | Yu et al. |
| 2017/0216499 | A1 | 8/2017 | Kaplan |
| 2017/0258988 | A1 | 9/2017 | Meyer et al. |
| 2018/0229055 | A1 | 8/2018 | Marsteller |
| 2018/0296855 | A1* | 10/2018 | Lohrenz ............... A61N 5/1017 |
| 2019/0240504 | A1 | 8/2019 | Brachman et al. |
| 2019/0259506 | A1 | 8/2019 | Vose et al. |
| 2019/0290643 | A1 | 9/2019 | Ni et al. |
| 2019/0336791 | A1 | 11/2019 | Shilton et al. |
| 2020/0101318 | A1 | 4/2020 | Marsteller |
| 2020/0171323 | A1 | 6/2020 | Marsteller et al. |
| 2020/0197725 | A1 | 6/2020 | Marsteller |
| 2022/0212032 | A1 | 7/2022 | Marsteller et al. |

FOREIGN PATENT DOCUMENTS

| | | | |
|---|---|---|---|
| DE | 1149134 | B | 5/1963 |
| EP | 1529554 | B1 | 2/2006 |
| EP | 1997532 | A1 | 12/2008 |
| EP | 3031494 | B1 | 8/2018 |
| FR | 4398 | E | 7/1905 |
| GB | 2551706 | A | 1/2018 |
| IN | 304392-0001 | | 3/2019 |
| IN | 315612-001-0001 | | 2/2020 |
| JP | S63138962 | A | 6/1988 |
| JP | 2001507969 | A | 6/2001 |
| JP | 2011508654 | A | 3/2011 |
| JP | 2016512101 | A | 4/2016 |
| JP | 2020533098 | A | 11/2020 |
| JP | D1733444 | | 12/2022 |
| RU | 134056 | U1 | 11/2013 |

(56)                    References Cited

FOREIGN PATENT DOCUMENTS

| WO | WO9850092 | 11/1998 |
|----|-----------|---------|
| WO | WO200158346 A1 | 8/2001 |
| WO | 2004098523 A2 | 11/2004 |
| WO | 2005079915 A1 | 9/2005 |
| WO | 2007106557 A2 | 9/2007 |
| WO | 2009075714 A1 | 6/2009 |
| WO | 2009149175 A1 | 12/2009 |
| WO | 2010022153 A1 | 2/2010 |
| WO | 2011053908 A1 | 5/2011 |
| WO | WO2013186779 A2 | 12/2013 |
| WO | 2014194959 A1 | 12/2014 |
| WO | WO2015057531 A2 | 4/2015 |
| WO | WO2015105539 A3 | 7/2015 |
| WO | WO2016178746 A1 | 11/2016 |
| WO | WO2017112891 A1 | 6/2017 |
| WO | WO2018060983 A1 | 4/2018 |
| WO | WO2019050863 A1 | 3/2019 |
| WO | 2019113192 A1 | 6/2019 |
| WO | WO2019164940 A1 | 8/2019 |
| WO | 2020113091 A1 | 6/2020 |

OTHER PUBLICATIONS

Acosta et. al., "A Newly Designed Glaucoma Drainage Implant Made of Poly(styrene-b-isobutylene-b-styrene)." Arch Opthalmol v. 124 (2006): 1742-1749, 8 pages.
Cabourne et al., "Mitomycin C versus 5-Fluorouracil for wound healing in glaucoma surgery." Cochrane Database of Systematic Reviews (2015), Issue 11. Art. No. CD006259, 52 pages.
Amano et al., "Comparative study of intraoperative mitomycin C and β irradiation in pterygium surgery" British Journal of Ophthalmology (2000) 84:618-621, 4 pages.
Khaw et al., "Trabeculectomy Technique." Glaucoma Today (2005) Mar./Apr. 22-29, 8 pages.
Khaw et. al., 2015, ARVO Poster Abstract, 2 pages.
Erickson et al. "The American College of Radiology and the American Brachytherapy Society practice parameter for the performance of radionuclide-based high-dose-rate brachytherapy." Brachytherapy 16.1 (2017): 75-84.
Cordeiro, M. F., L. Chang, and P. T. Khaw. "The healing of ocular tissues: The basis of successful treatment of ocular disease." (2000): 101-110.
Kung JS et al: "Cataract Surgery in the Glaucoma Patient", Middle East African Journal of Ophthalmology, vol. 22, No. 1, Mar. 31, 2015 (Mar. 31, 2015), pp. 10-17.
Schultz et al. "Growth factors and ocular wound healing." Eye 8.2 (1994): 184-187.
Kirwan et al. "Beta irradiation: new uses for an old treatment: a review." Eye 17.2 (2003): 207-215.
Khaw et al. "Modulation of wound healing after glaucoma surgery." Current opinion in ophthalmology 12.2 (2001): 143-148.
Sanoculis LTD, MIMS Procedure. http://www.sanoculis.com/category/mims-procedure (2014) 2 pages.
Kumar et al. Minimally invasive micro sclerostomy may be alternative to trabeculectomy. Ocular Surgery News U.S. Edition, May 10, 2016, 4 pages.
Cook et al. "Randomised clinical trial of trabeculectomy with mitomycin-C versus trabeculectomy with beta radiation." South African Ophthalmology Journal 13.4 (2018): 11-14.
Egbert, "Glaucoma in West Africa: a neglected problem." British journal of ophthalmology 86.2 (2002): 131-132.
Khaw et al. "Effect of beta radiation on proliferating human Tenon's capsule fibroblasts." British journal of ophthalmology 75.10 (1991): 580-583.
Wilder, el. al. "Pterygium treated with excision and postoperative beta irradiation." International Journal of Radiation Oncology* Biology* Physics 23.3 (1992): 533-537.
Kirwan et al. "Beta radiation in glaucoma surgery (Review)" Cochrane Database of Systematic Reviews (2012).

G Hay-Smith et al. "Beta radiation: an effective and potentially cheap aid to preventing sight loss from glaucoma, 2010." Conference proceedings. 3 pages.
Lai et al. "Trabeculectomy with β radiation: Long-term follow-up." Ophthalmology 110.9 (2003): 1822-1826.
Quigley et al. "The number of people with glaucoma worldwide in 2010 and 2020." British journal of ophthalmology 90.3 (2006): 262-267.
Mpyet et al. "Site of trabeculectomy and control of intraocular pressure: a preliminary report." Nigerian Journal of Surgical Research 4.3 (2002): 94-97.
Kirwan et al. "Effect of β radiation on success of glaucoma drainage surgery in South Africa: randomised controlled trial." Bmj 333.7575 (2006): 942.
George et al. "Glaucoma in India: estimated burden of disease." Journal of glaucoma 19.6 (2010): 391-397.
Venkatesh et al. "Glaucoma care in India." Glaucoma Today (2013): 37-39.
Dhalla et al. "Is beta radiation better than 5 flurouracil as an adjunct for trabeculectomy surgery when combined with cataract surgery? A randomised controlled trial." PloS one 11.9 (2016): e0161674.
George et al. "Prevalence of glaucoma in India: a review." J Curr Glaucoma Pract 1.2 (2007): 7-11.
Technical Information and Instruction Manual for users of Beta Therapy Source Model 67-850, Nuclear Associates, Carle Place, NY. Copyright 1979, 14 pages.
Soares "Comparison of NIST and manufacturer calibrations of 90Sr+ 90Y ophthalmic applicators." Medical Physics 22.9 (1995): 1487-1493.
Bahrassa et al "Postoperative beta radiation treatment of pterygium." International Journal of Radiation Oncology* Biology* Physics 9.5 (1983): 679-684.
Castroviejo. "New masks to limit the active surface of radiation in beta ray applicators." Transactions-American Academy of Ophthalmology and Otolaryngology. American Academy of Ophthalmology and Otolaryngology 60.3 (1956): 486.
Zhang et al., "In vivo cross-sectional observation and thickness measurement of bulbar conjunctiva using optical coherence tomography." Investigative ophthalmology & visual science 52.10 (2011): 7787-7791.
Wells et al. "Comparison of two clinical bleb grading systems." Ophthalmology 113.1 (2006): 77-83.
Dhingra et al. "The moorfields safer surgery system." Middle East African journal of ophthalmology 16.3 (2009): 112.
Constable et al. "The effects of single doses of β radiation on the wound healing behaviour of human Tenon's capsule fibroblasts." British journal of ophthalmology 88.2 (2004): 169-173.
Assmann et al. "Biodegradable radioactive implants for glaucoma filtering surgery produced by ion implantation." Nuclear Instruments and Methods in Physics Research Section B: Beam Interactions with Materials and Atoms 257.1-2 (2007): 108-113.
Ayyala et al, Early Follow-Up after Xen Implantation Needed. Ocular Surgery News U.S. Edition, Mar. 5, 2018, 1 page.
Ayyala et al , Xen Gel Stent Early Results: Safety and Efficacy in the Short Term. AGS 2018 Annual Meeting. Mar. 4, 2 pages.
Howlet et al., "Bulbar conjunctival and Tenon's layer thickness measurement using optical coherence tomography." Journal of current glaucoma practice 8.2 (2014): 63.
NRC "Information Notice 96-66: Recent Misadminitrations Caused by Incorrect Calibrations of Strontium-90 Eye Applicators", United States Nuclear Regulatory Commission, Office of Nuclear Material Safety and Safeguards, Washington D.C. 20555, Dec. 13, 1996, 4 pages.
Nilsen, PhD, Department of Physics and Scientific Computing Group University of Oslo, N-0316 Oslo, Norway in Spring 2008, 14 pages.
Kirwan et al. "Beta radiation in glaucoma surgery" 2012, 2 pages.
J.E. Gentle, Monte Carlo Methods in Statistics, International Encyclopedia of Education (Third Edition) 2010.
"Radiance Therapeutics: CEO Laurence Marsteller presenting at Eyecelerator 2022." Found online at youtube.com. Mar. 16, 2023. Reference dated Oct. 18, 2022. Retrieved from https://www.youtube.com/watch?v=sdkOXVcibF4.

(56) References Cited

OTHER PUBLICATIONS

"Physics world: Novel brachytherapy device treats eye cancer with intensity-modulated radiation." Found online at physicsworld.com. Mar. 16, 2023. Reference dated Jun. 17, 2021. Retrieved from https://physicsworld.com/a/.novel-brachytherapy-device-treats-eye-cancer-with-intensity-modulated-radiation/.

"Fastener Superstore: Standard blind rivets." Found online at amazon.com. Mar. 16, 2023. Reference dated Jan. 30, 2008. Retrieved from https://www.amazon.com/Standard-Blind-Rivets-Aluminum-Carton/dp/B005EY8550.

"Ali Express: Titanium Kuglen Iris Hook and Lens Manipulator." Found online at aliexpress.com. Mar. 16, 2023. Reference dated Nov. 30, 2022. Retrieved from https://www.aliexpress.us/item/2255800223699318.html?.

* cited by examiner

100

200

A

B

C

D

300

400

FIG. 2A
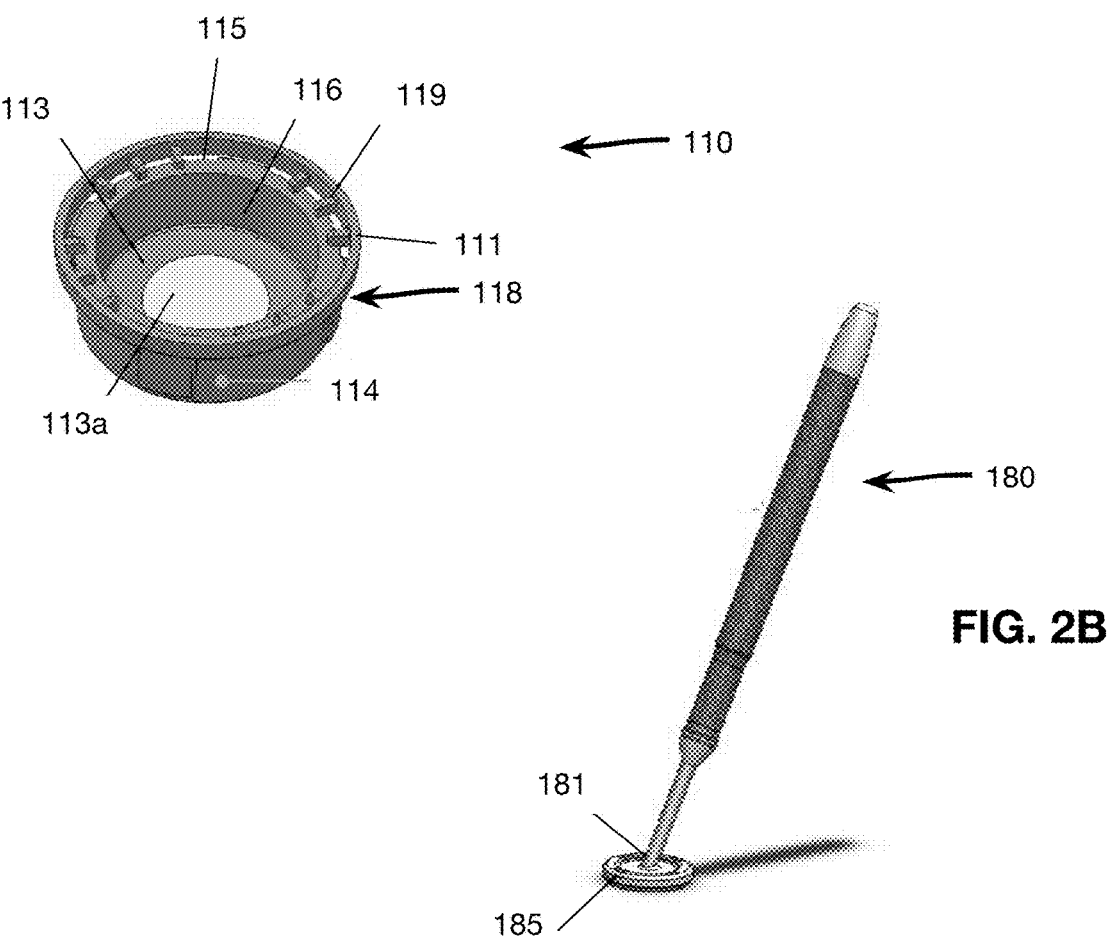
FIG. 2B
FIG. 2C
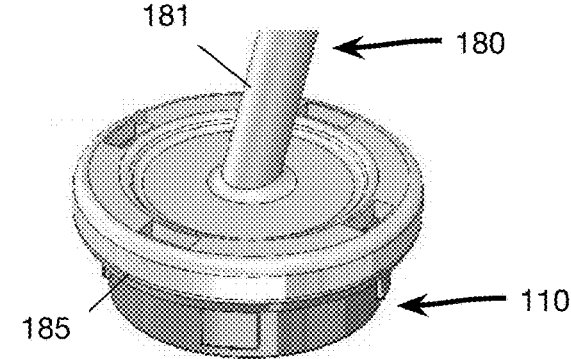

185

130

110

111

185

115

130

112

132

101

114

111

196

194

185

213    216    214

← 210

215

213a     218

280

281

285

281    280

291

285

297

FIG. 7A
FIG. 7B
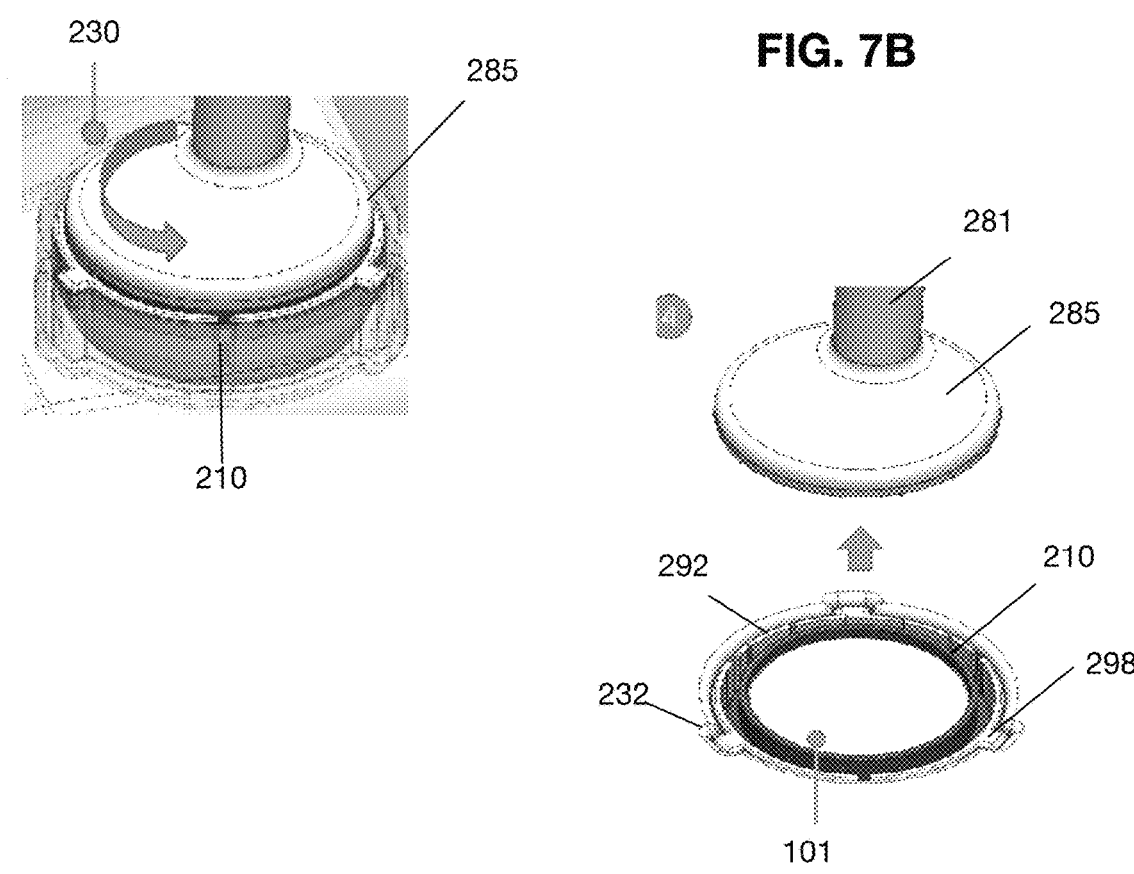
FIG. 7C
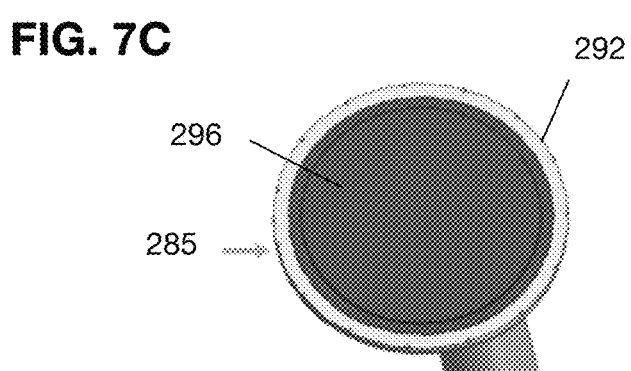

FIG. 8A
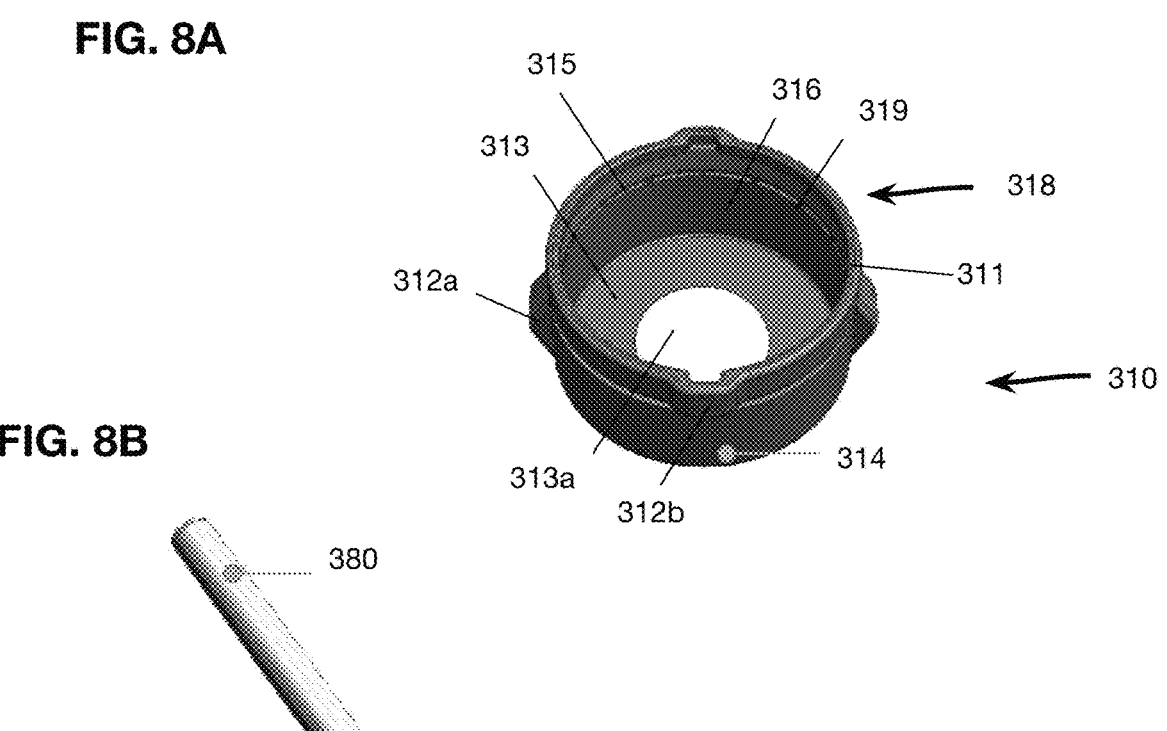
FIG. 8B
FIG. 8C
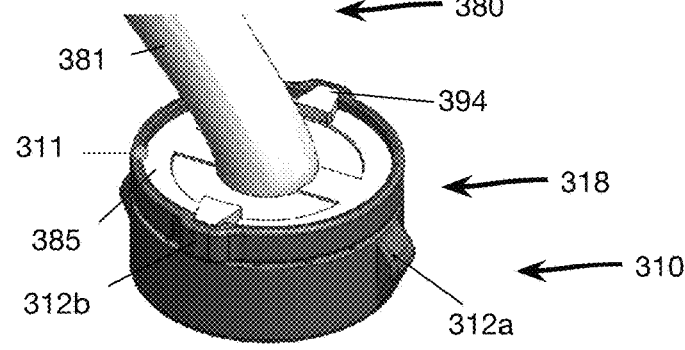

391 381 394 385
392 396

311 318
319
316 310
312 314
313

396
394 385

196 31
312b 394
314
313 313a 101

391
394
396

FIG. 13A
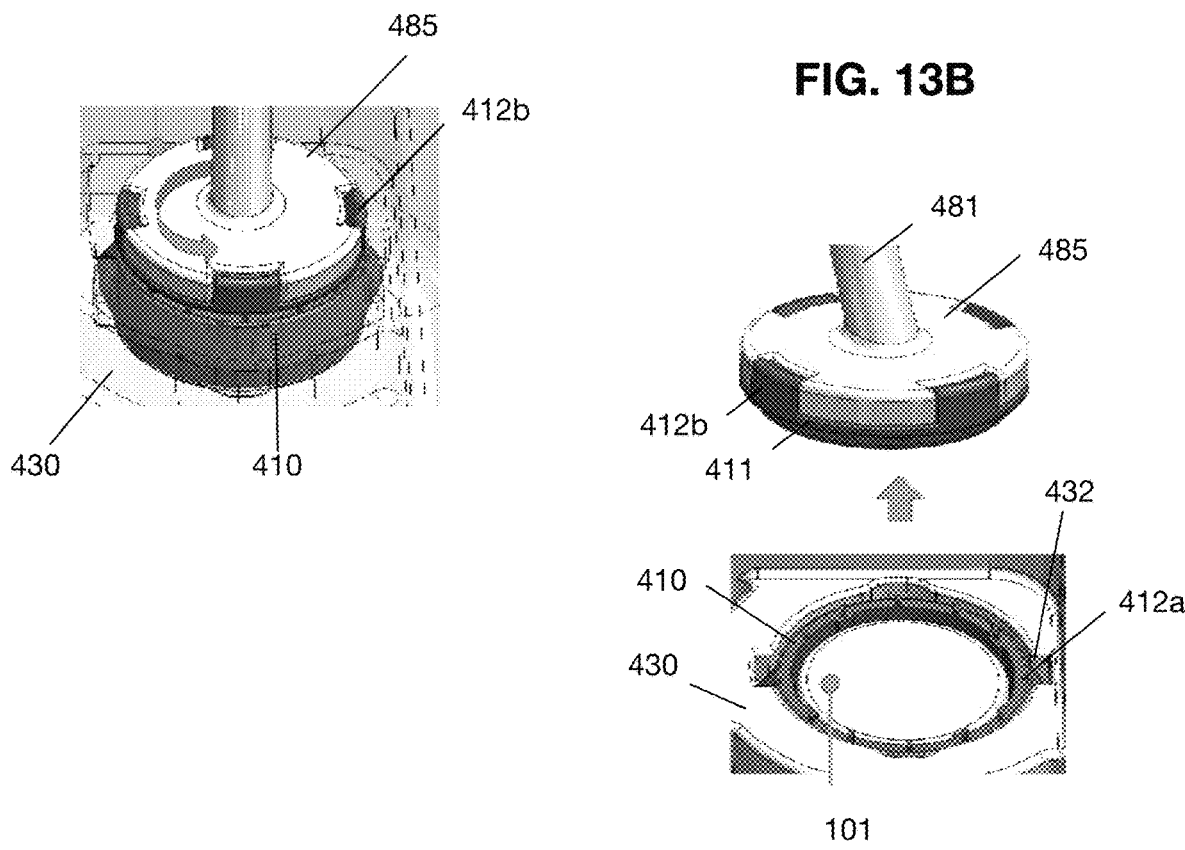
FIG. 13B
FIG. 13C
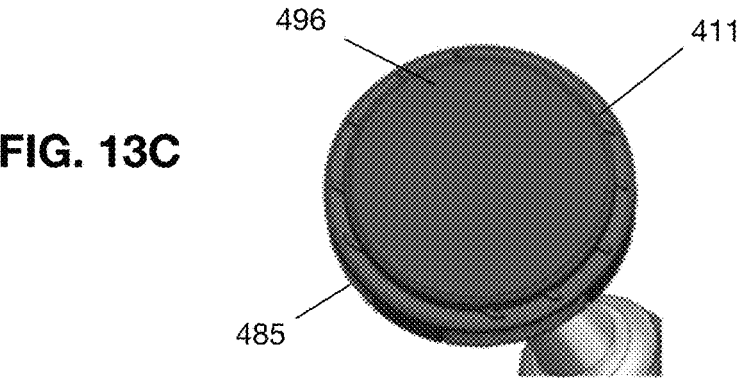

SYSTEM FOR BRACHYTHERAPY

CROSS-REFERENCES TO RELATED APPLICATIONS

This application is a continuation-in-part of and claims priority to PCT Application No. PCT/US2020/047235 filed on Aug. 20, 2020, which claims priority to U.S. Provisional Patent Application No. 62/889,461 filed on Aug. 20, 2019, the specification(s) of which is/are incorporated herein in their entirety by reference.

This application is a continuation-in-part of and claims priority to PCT Application No. PCT/US2021/064141 filed on Dec. 17, 2021, which is a continuation-in-part of and claims priority to PCT Application No. PCT/US2021/012694 filed on Jan. 8, 2021 and PCT Application No. PCT/US2021/012744 filed on Jan. 8, 2021, and also claims priority to U.S. Provisional Patent Application No. 63/126,855 filed on Dec. 17, 2020, the specification(s) of which is/are incorporated herein in their entirety by reference.

This application is a continuation-in-part of and claims priority to PCT Application No. PCT/US2021/064190 filed on Dec. 17, 2021, which is a continuation-in-part of and claims priority to PCT Application No. PCT/US2021/012694 filed on Jan. 8, 2021 and PCT Application No. PCT/US2021/012744 filed on Jan. 8, 2021, and also claims priority to U.S. Provisional Patent Application No. 63/126,855 filed on Dec. 17, 2020, the specification(s) of which is/are incorporated herein in their entirety by reference.

This application is a continuation-in-part of and claims priority to PCT Application No. PCT/US2020/063435 filed on Dec. 4, 2020, which claims priority to U.S. Provisional Patent Application No. 62/944,952 filed on Dec. 6, 2019, the specification(s) of which is/are incorporated herein in their entirety by reference.

This application is a continuation-in-part of and claims priority to PCT Application No. PCT/US2021/012744 filed on Jan. 08, 2021, which claims priority to U.S. Provisional Patent Application No. 62/958,554 filed on Jan. 8, 2020, the specification(s) of which is/are incorporated herein in their entirety by reference.

This application is a continuation-in-part of and claims priority to PCT Application No. PCT/US2021/012694 filed on Jan. 8, 2021, which claims priority to U.S. Provisional Patent Application No. 62/958,517 filed Jan. 8, 2020 and U.S. Provisional Patent Application No. 62/958,634 filed Jan. 8, 2020, the specification(s) of which is/are incorporated herein in their entirety by reference.

This application is a continuation-in-part of and claims priority to U.S. patent application Ser. No. 16/698,676 filed on Nov. 27, 2019, which claims priority to U.S. Provisional Patent Application No. 62/772,741 filed on Nov. 29, 2018, the specification(s) of which is/are incorporated herein in their entirety by reference.

This application is a continuation-in-part of and claims priority to U.S. patent application Ser. No. 16/584,737 filed Sep. 26, 2019, which claims priority to U.S. Provisional Patent Application No. 62/738,573 filed on Sep. 28, 2018, and is also a continuation-in-part and claims priority to PCT Application No. PCT/US2018/049400 filed on Sep. 4, 2018, which claims priority to GB Application No. 1714392.6 filed Sep. 7, 2017, the specification(s) of which is/are incorporated herein in their entirety by reference.

This application is a continuation-in-part of and claims priority to U.S. patent application Ser. No. 16/810,204 filed Mar. 5, 2020, which is a continuation-in-part and claims priority to PCT Application No. PCT/US2018/049400 filed on Sep. 4, 2018, which claims priority to GB Application No. 1714392.6 filed Sep. 7, 2017, the specification(s) of which is/are incorporated herein in their entirety by reference.

BACKGROUND OF THE INVENTION

Field of the Invention

The present invention relates to brachytherapy devices, including but not limited to to single-use brachytherapy devices wherein the device is rendered useless, e.g., the device cannot be re-used in the same manner, unless components of the device are repaired.

Background Art

Brachytherapy is a type of radiation therapy that involves placing a radiation source directly on a target tissue. The present invention features brachytherapy systems, such as but not limited to single-use brachytherapy systems. As an example, the single-use brachytherapy systems herein may feature a cap into which a radionuclide brachytherapy source (RBS) can be inserted and a handle that removably attaches to the cap. When the handle is removed/disassembled from the cap in order to access the RBS, the system is rendered useless, e.g., the system cannot be re-used in the same manner (e.g., the system does not allow re-engagement of the handle and cap in the same manner), unless the system is repaired.

BRIEF SUMMARY OF THE INVENTION

The present invention describes single-use brachytherapy systems for the application or use of a radionuclide brachytherapy source (RBS). The present invention describes several specific examples of single-use systems; however, the present invention is not limited to the specific embodiments herein.

Briefly, the systems herein may feature a cap for holding a radionuclide brachytherapy source (RBS) and a handle that engages the cap. When the system is disassembled, e.g., when the handle is removed from the cap in order to access the RBS, the system is rendered useless, e.g., the system cannot be re-used in the same manner (e.g., the system does not allow re-engagement of the handle and cap in the same manner), unless the system is repaired. For example, single-use brachytherapy systems here may comprise a cap with an internal cavity for accepting a radionuclide brachytherapy source (RBS); a handle comprising a handle coupling portion at a distal end for attaching to the cap; and a cap coupling portion disposed on the cap for engaging the handle coupling portion. The handle coupling portion and cap coupling portion engage to house the RBS in the internal cavity of the cap, and disengagement of the handle coupling portion and cap coupling portion alter the handle coupling portion, the cap coupling portion, or both the handle coupling portion and the cap coupling portion so as to render the system useless (e.g., unable to re-used in the same manner unless repaired), e.g., the handle coupling portion and cap coupling portion cannot be re-engaged as was previously done. For example, the handle coupling portion becomes terminally detached from the cap coupling portion, unless repaired.

When the handle coupling portion and cap coupling portion engage to house the RBS in the internal cavity of the cap, in certain embodiments the internal cavity may be sealed, e.g., engaging the handle coupling portion and cap coupling portion may form a particular barrier and/or a liquid barrier, or other type of barrier. The barrier, e.g., the particular barrier and/or the liquid barrier may help prevent particles and/or liquids or other molecules from entering into the internal cavity or exiting the internal cavity. The present invention is not limited to a particular type of seal formed by the engagement of the cap coupling portion and the handle coupling portion.

In certain embodiments, the system further comprises a tray. The tray may function to hold and/or store one or more components such as but not limited to the cap, the handle, an accessory, etc. The tray may function as a fixture to hold the cap (or the cap and a portion of the handle, e.g., the cap and the handle coupling portion) while the system is assembled or disassembled. For example, in certain embodiments, the tray comprises a slot for accepting the cap (or cap and handle coupling portion), wherein the slot is configured to prevent the cap (or cap and handle coupling portion) from rotating in a clockwise and counterclockwise direction. In certain embodiments, tabs are disposed on the cap and/or the handle coupling portion; the tabs can slide or align into the slot in the tray, and the tabs (restrained by the configuration of the slot into which the cap and/or handle coupling portion is inserted) prevent the cap (or cap and handle coupling portion from rotating in a clockwise and counterclockwise direction. In certain embodiments, the tray further comprises a slot for storing the handle. In certain embodiments, the tray further comprises a slot for storing one or more accessories.

In certain embodiments, disengagement of the system (e.g., disengagement of the handle and cap to allow access to the radionuclide brachytherapy source (RBS) in the internal cavity of the cap) features immobilizing the cap (or the cap and the handle coupling portion) and twisting or rotating the handle with respect to the cap (or cap and handle coupling portion). In certain embodiments, disengagement of the system (e.g., disengagement of the handle and cap to allow access to the radionuclide brachytherapy source (RBS) in the internal cavity of the cap) features immobilizing the cap (or the cap and the handle coupling portion), pushing the handle downwardly (e.g., in the direction of the cap (or cap and handle coupling portion), and twisting or rotating the handle with respect to the cap (or cap and handle coupling portion). In certain embodiments, disengagement of the system (e.g., disengagement of the handle and cap to allow access to the radionuclide brachytherapy source (RBS) in the internal cavity of the cap) features immobilizing the cap (or the cap and the handle coupling portion) and pushing the handle downwardly (e.g., in the direction of the cap (or cap and handle coupling portion). In certain embodiments, an accessory is used to rotate the handle, e.g., an accessory such as a lever arm, winding key, T-bar, etc. is attached to the handle and rotated or moved in a particular manner so as to translate the motion to the handle, thereby disengaging the system. The present invention is not limited to the aforementioned methods for disengaging the system.

The single-use brachytherapy systems herein may comprise a cap with an internal cavity for temporarily accepting a radionuclide brachytherapy source; a handle comprising a handle coupling portion at a distal end for temporarily attaching to the cap; and a cap coupling portion disposed on the cap for engaging the handle coupling portion. In certain embodiments, the handle coupling portion comprises a snap cavity disposed on a bottom surface, and the cap coupling portion comprises a ring and a plurality of attachment ribs that attach the ring to a top surface of a side wall of the cap. The handle coupling portion and cap coupling portion can engage to house a radionuclide brachytherapy source (RBS) in the internal cavity as the ring of the cap snaps into the snap cavity of the handle coupling portion. Disengagement of the handle coupling portion and cap coupling portion alters the handle coupling portion, the cap coupling portion, or both the handle coupling portion and the cap coupling portion. The alteration of the cap coupling portion, handle coupling portion, or both renders the system useless, e.g., the system cannot be re-used in the same manner (e.g., the system does not allow re-engagement of the handle and cap in the same manner, the handle coupling portion and cap coupling portion cannot be re-engaged as was previously done), unless the system is repaired.

The single-use brachytherapy systems herein may comprise a cap with an internal cavity for temporarily accepting a radionuclide brachytherapy source; a handle comprising a handle coupling portion at a distal end for temporarily attaching to the cap, and a cap coupling portion disposed on the cap for engaging the handle coupling portion. In certain embodiments, the cap coupling portion comprises one or more protrusions extending outwardly from an outer surface of a side wall of the cap. In certain embodiments, the handle coupling portion comprises a snap cavity for accepting the cap. The handle coupling portion and cap coupling portion engage to house a radionuclide brachytherapy source (RBS) in the internal cavity as the protrusions of the cap coupling portion lock inside the snap cavity of the handle coupling portion. Disengagement of the handle coupling portion and cap coupling portion alters the handle coupling portion, the cap coupling portion, or both the handle coupling portion and the cap coupling portion. The alteration of the cap coupling portion, handle coupling portion, or both, renders the system useless, e.g., the system cannot be re-used in the same manner (e.g., the system does not allow re-engagement of the handle and cap in the same manner, the handle coupling portion and cap coupling portion cannot be re-engaged as was previously done), unless the system is repaired.

In certain embodiments, the system further comprises the RBS.

The present invention also features a single-use brachytherapy system comprising a radionuclide brachytherapy source (RBS); a cap with an internal cavity; a handle comprising a handle coupling portion at a distal end for attaching to the cap; and a cap coupling portion disposed on the cap for engaging the handle coupling portion. The handle coupling portion and cap coupling portion are engaged to house the RBS in the internal cavity. The handle coupling portion, the cap coupling portion, or both the handle coupling portion and cap coupling portion are configured to be altered by disengagement of the handle and cap for providing access the RBS for its removal from the inner cavity of the cap, wherein said altering of the handle coupling portion, cap coupling portion, or both the handle coupling portion and cap coupling portion causes the handle and cap to be unable to re-engage.

The present invention also features methods of preparing a single-use brachytherapy system according to the present invention. In certain embodiments, the method comprises inserting a radionuclide brachytherapy source (RBS) into the internal cavity of the cap; and engaging the handle coupling portion and cap coupling portion to secure the RBS in the internal cavity of the cap. The handle coupling portion, the cap coupling portion, or both the handle coupling portion and cap coupling portion are configured to be altered by disengagement of the handle and cap for providing access the RBS for its removal from the inner cavity of the cap, wherein said altering of the handle coupling portion, cap coupling portion, or both the handle coupling portion and cap coupling portion causes the handle and cap to be unable to re-engage.

The present invention also features a method of preparing and disengaging a single-use brachytherapy system according to the present invention. The method may comprise inserting a radionuclide brachytherapy source (RBS) into the internal cavity of the cap; engaging the handle coupling portion and cap coupling portion to secure the RBS in the internal cavity of the cap; and disengaging the handle and the cap to provide access to the RBS in the internal cavity of the cap, wherein disengaging the handle and cap causes alteration of the handle coupling portion, the cap coupling portion, or both the handle coupling portion such that the handle and cap are unable to re-engage.

In some embodiments, disengaging the handle and the cap comprises immobilizing the cap and applying pressure to the cap via the handle. In some embodiments, disengaging the handle and the cap comprises immobilizing the cap and twisting the handle in a clockwise or counterclockwise direction. In some embodiments, disengaging the handle and the cap comprises immobilizing the cap, applying pressure to the cap via the handle, and twisting the handle in a clockwise or counterclockwise direction.

The present invention also includes methods introducing radiation to a target using the systems disclosed herein. For example, the methods may feature applying the system by contacting the bottom surface of the cap to a target tissue.

As used herein, the term "window" may refer to an area or portion of the bottom surface of the cap that may be open or closed (e.g., sealed with the bottom surface of the cap). The window may be constructed from a material such as but not limited to a translucent or visibly opaque material. The window may purposefully or intentionally alter the emission of radiation from the radionuclide brachytherapy source (RBS) in a particular manner, e.g., in a particular pattern. The window is not limited to the aforementioned configurations, materials, or purposes.

As used herein, the term "useless" refers to the inability of the system to be used again in the same manner without repairing the alterations caused to the system when the handle and cap were disengaged in order to remove the radionuclide brachytherapy source (RBS) from the internal cavity of the cap. For example, after the use of the system, disengagement of the handle and cap for RBS removal causes the handle coupling portion, the cap coupling portion, or both to be altered in a way that does not allow re-engagement of the handle and cap in the same exact manner without repair of the handle coupling portion, cap coupling portion, or both.

The present invention provides examples of single-use brachytherapy devices and is not limited to said examples. The present invention includes any appropriate brachytherapy device configuration that provides for alteration of the device after use such that the alteration prevents re-use of the device in the exact manner it was previously used, unless repaired.

The present invention features a brachytherapy system comprising a cap with an internal cavity for accepting a radionuclide brachytherapy source (RBS); a handle comprising a handle coupling portion at a distal end for attaching to the cap; and a cap coupling portion disposed on the cap for engaging the handle coupling portion. In some embodiments, the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

In some embodiments, the handle coupling portion comprises a tab lock, and the cap coupling portion comprises a tab that protrudes upwardly from the cap and can snap into the tab lock of the handle; wherein the handle coupling portion and cap coupling portion are configured to engage in a first position wherein the tab is engaged with the tab lock so as to house and secure the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

In some embodiments, the cap coupling portion comprises a ring attached to a top surface of the cap via one or more attachment ribs, and the handle coupling portion is configured to snap onto the ring, and disengagement of the handle coupling portion and cap coupling portion results in the shearing of the attachment ribs and the ring remains snapped onto the handle coupling portion.

In some embodiments, the handle coupling portion comprises a snap cavity disposed on a bottom surface; and the cap coupling portion comprises a ring and a plurality of attachment ribs that attach the ring to a top surface of a side wall of the cap. In some embodiments, the handle coupling portion and cap coupling portion can engage to house the RBS in the internal cavity as the ring is configured to snap into the snap cavity of the handle coupling portion, and disengagement of the handle coupling portion and cap coupling portion alters the handle coupling portion, the cap coupling portion, or both the handle coupling portion and the cap coupling portion such that the handle coupling portion and cap coupling portion cannot re-engage as was previously done.

In some embodiments, the handle coupling portion comprises a snap cavity for accepting the cap, and the cap coupling portion comprises one or more protrusions extending outwardly from an outer surface of a side wall of the cap. In some embodiments, the handle coupling portion and cap coupling portion engage to house the RBS in the internal cavity as the protrusions of the cap coupling portion are configured to lock inside the snap cavity of the handle coupling portion, and disengagement of the handle coupling portion and cap coupling portion alters the handle coupling portion, the cap coupling portion, or both the handle coupling portion and the cap coupling portion such that the handle coupling portion and cap coupling portion cannot re-engage as was previously done.

The present invention also features a brachytherapy system comprising a cap with an internal cavity for accepting a radionuclide brachytherapy source (RBS); a handle comprising a handle coupling portion at a distal end for attaching to the cap, the handle coupling portion comprises a tab lock; and a cap coupling portion disposed on the cap for engaging the handle coupling portion, the cap coupling portion comprises a tab that protrudes upwardly from the cap and can snap into the tab lock of the handle. In some embodiments, the handle coupling portion and cap coupling portion are configured to engage in a first position wherein the tab is engaged with the tab lock so as to house and secure the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

The present invention also features a brachytherapy system comprising a radionuclide brachytherapy source (RBS); a cap with an internal cavity for accepting a radionuclide brachytherapy source (RBS); a handle comprising a handle coupling portion at a distal end for attaching to the cap; and a cap coupling portion disposed on the cap for engaging the handle coupling portion. In some embodiments, the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

In some embodiments, the cap coupling portion comprises a ring attached to a top surface of the cap via one or more attachment ribs, and the handle coupling portion is configured to snap onto the ring, and disengagement of the handle coupling portion and cap coupling portion results in the shearing of the attachment ribs and the ring remains snapped onto the handle coupling portion.

In some embodiments, the handle coupling portion comprises a snap cavity disposed on a bottom surface; and the cap coupling portion comprises a ring and a plurality of attachment ribs that attach the ring to a top surface of a side wall of the cap; wherein the handle coupling portion and cap coupling portion can engage to house the RBS in the internal cavity as the ring is configured to snap into the snap cavity of the handle coupling portion, and disengagement of the handle coupling portion and cap coupling portion alters the handle coupling portion, the cap coupling portion, or both the handle coupling portion and the cap coupling portion such that the handle coupling portion and cap coupling portion cannot re-engage as was previously done.

In some embodiments, the handle coupling portion comprises a snap cavity for accepting the cap, and the cap coupling portion comprises one or more protrusions extending outwardly from an outer surface of a side wall of the cap; wherein the handle coupling portion and cap coupling portion engage to house the RBS in the internal cavity as the protrusions of the cap coupling portion are configured to lock inside the snap cavity of the handle coupling portion, and disengagement of the handle coupling portion and cap coupling portion alters the handle coupling portion, the cap coupling portion, or both the handle coupling portion and the cap coupling portion such that the handle coupling portion and cap coupling portion cannot re-engage as was previously done.

In some embodiments, the handle coupling portion comprises a tab lock, and the cap coupling portion comprises a tab that protrudes upwardly from the cap and can snap into the tab lock of the handle; wherein the handle coupling portion and cap coupling portion are configured to engage in a first position wherein the tab is engaged with the tab lock so as to house and secure the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 2A shows a detailed view of the cap of System A.

FIG. 2B shows a detailed view of the handle of System A.

FIG. 2C shows a detailed view of the cap engaged with the handle of System A.

FIG. 7A shows an in-use view of System B.

FIG. 7B shows an in-use view of System B.

FIG. 7C shows a bottom view of the handle engagement component of System B.

FIG. 8A shows a detailed view of the cap of System C.

FIG. 8B shows a detailed view of the handle of System C.

FIG. 8C shows a detailed view of the cap engaged with the handle of System C.

FIG. 13A shows an in-use view of System D.

FIG. 13B shows an in-use view of System D.

FIG. 13C shows a bottom view of the handle engagement component of System D.

DETAILED DESCRIPTION OF THE INVENTION

Figure 1:
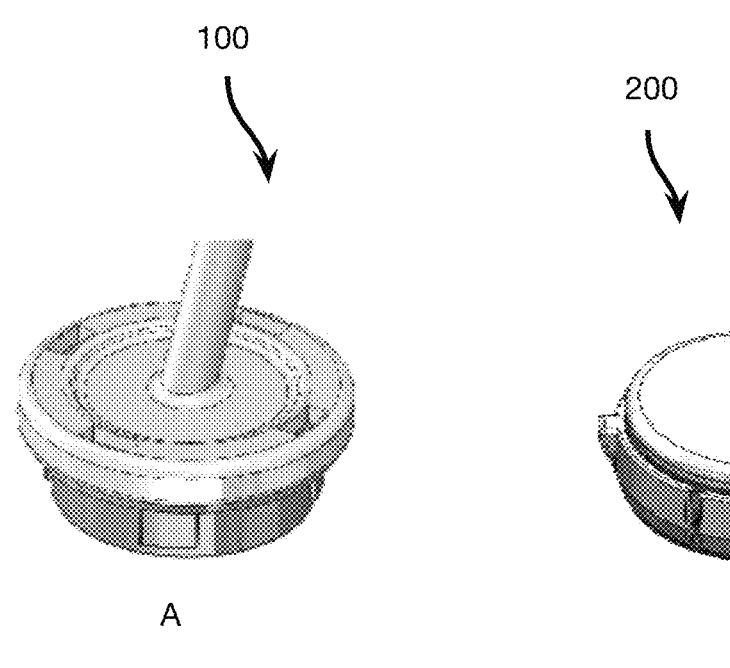
FIG. 1 shows a perspective view of four non-limiting examples of the brachytherapy systems of the present invention, System A, System B, System C, and System D.
Figure 1:
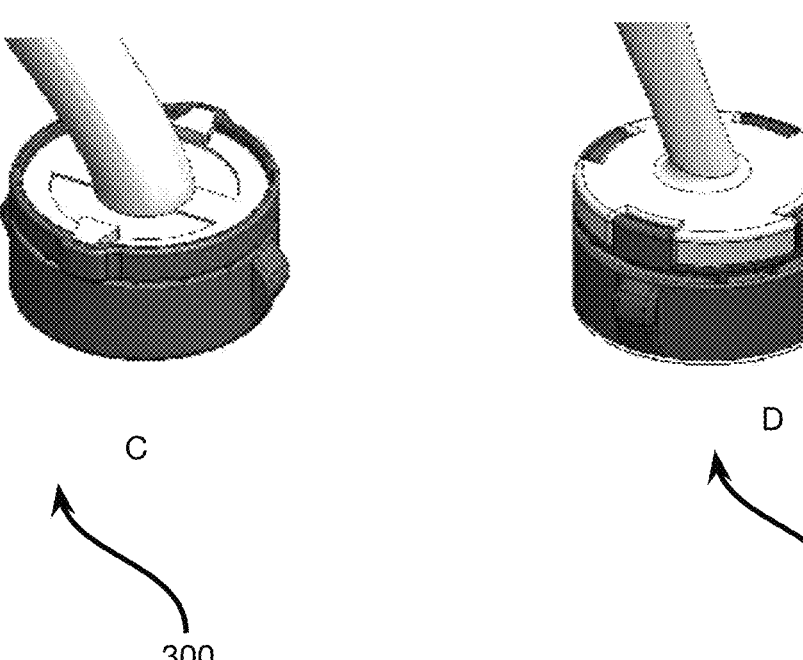

The present invention features single-use brachytherapy systems, e.g., systems for applying radiation to a surface, such as but not limited to the surface of the eye.

The single-use brachytherapy systems herein feature a cap into which an RBS can be inserted and a handle that removably attaches to the cap. When the handle is removed/ disassembled from the cap in order to access the RBS, the system is rendered useless, e.g., the system cannot be re-used in the same manner (e.g., the system does not allow re-engagement of the handle and cap in the same manner), unless the system is repaired.

System A

Referring to FIG. 2A and FIG. 2B, System A (100) features a cap (110) with an internal cavity (116) for temporarily housing an RBS (101). The cap may be disc-shaped (circular if viewed from the bottom) as shown; however, the cap (110) is not limited to any particular shape and may be rounded, oval, etc. The cap (110) has a bottom surface (113) and a side wall (114). The top of the cap (opposite the bottom surface (113) is open at least partially so as to allow insertion of the RBS (101) into the internal cavity (116). The bottom surface (113) may comprise a window (113*a*); however, the bottom surface (113) does not necessarily comprise a window (113*a*).

Disposed on the top edge (115) of the side wall (114) of the cap (110) is a cap coupling portion (118). The cap coupling portion (118) is for engaging the handle (180) as is described herein. A non-limiting example of a cap coupling portion is shown in FIG. 2A. The cap coupling portion (118) comprises a ring (111) and a plurality of attachment ribs (119) that attach the ring to the top surface (115) of the side wall (114) of the cap (110). The attachment ribs (119) are spaced apart, and are not limited to the configuration shown in FIG. 2A.

Referring to FIG. 2B, the system (100) further comprises a handle (180) having a distal end (181) to which a handle coupling portion (185) is disposed. The handle coupling portion (185) engages the cap coupling portion (118) of the cap (110). Once the cap coupling portion (118) and the handle coupling portion (185) engage and click together or lock together, the coupling portions (118, 185) cannot be disengaged without alteration of one or both of the coupling portions (118, 185). FIG. 2C shows the handle coupling portion (185) of the handle (180) attached to the cap (110).

The handle (180), e.g., the distal portion (181) of the handle, is attached to the handle coupling portion (185) at an angle, e.g., an angle formed by (i) the line of the handle (180) and (ii) the plane of the handle coupling portion (185), e.g., the plane of the top surface (191) of the handle coupling portion (185). As shown in FIG. 2B, the angle may be less than 90 degrees. In certain embodiments, the handle (180) is perpendicularly attached to the handle coupling portion (185), e.g., the angle is 90 degrees. In certain embodiments, the angle is from 10 to 20 degrees. In certain embodiments, the angle is from 20 to 30 degrees. In certain embodiments, the angle is from 30 to 40 degrees. In certain embodiments, the angle is from 40 to 50 degrees. In certain embodiments, the angle is from 50 to 60 degrees. In certain embodiments, the angle is from 60 to 70 degrees. In certain embodiments, the angle is from 70 to 80 degrees. In certain embodiments, the angle is from 80 to 90 degrees. In certain embodiments, the angle is from 45 to 90 degrees. In certain embodiments, the angle is from 60 to 90 degrees.

Figure 3A:
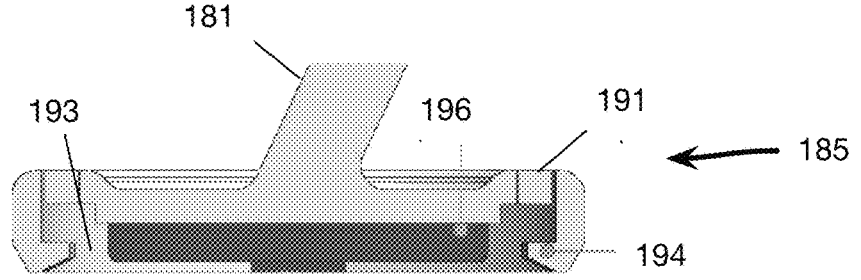
FIG. 3A shows a cross sectional view of the handle and cap of System A.
Figure 3A:
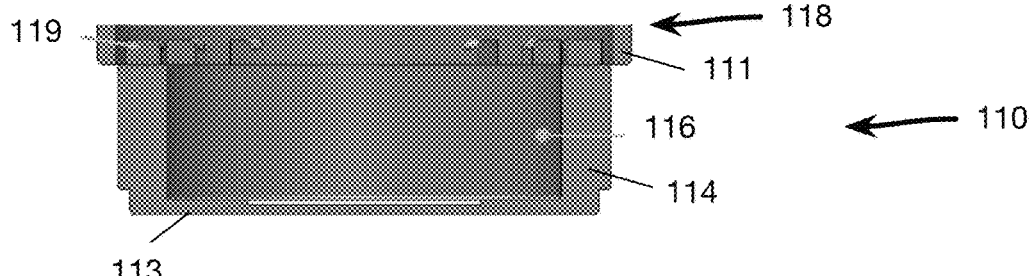
Figure 3B:
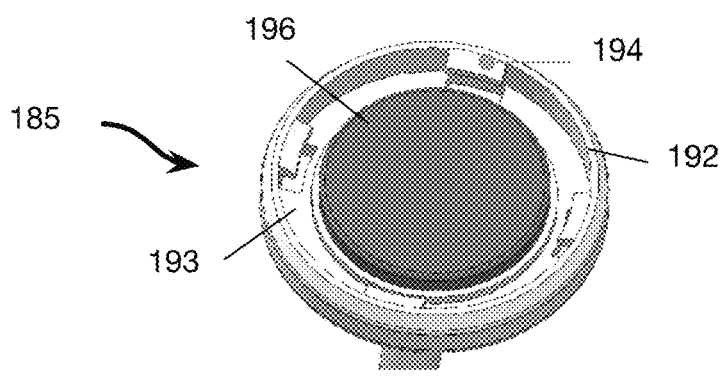
FIG. 3B shows a bottom view of the handle engagement component of System A.

FIG. 3A shows a cross sectional view of the handle coupling portion (185) of the handle (180) and the cap (110). The handle coupling portion (185) has a top surface (191) and a bottom surface (192). A snap cavity (193) is disposed in the bottom surface (192) into which the cap (110), e.g., the cap coupling portion (118) of the cap (110), can be inserted. As shown in FIG. 3A and FIG. 3B, the handle coupling portion (185) features one or more protrusions (194) that extend into the snap cavity (193).

Figure 3C:
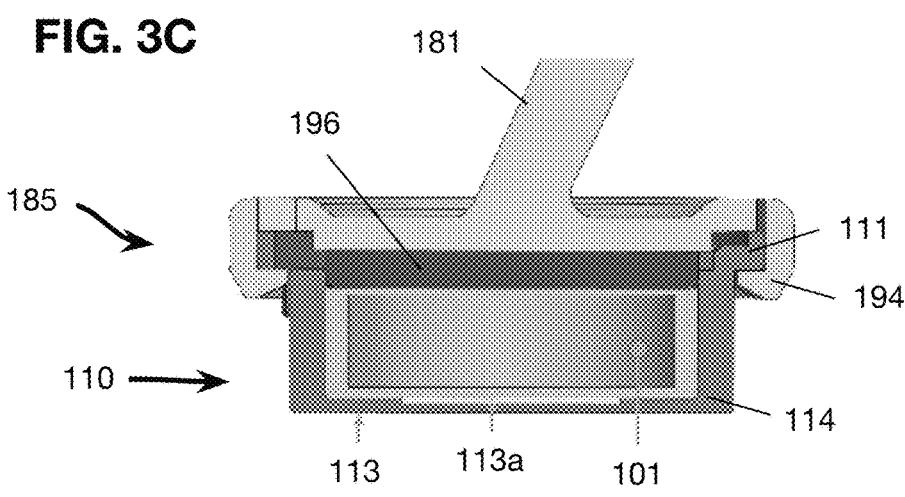
FIG. 3C shows a cross sectional view of the handle and cap of System A.

FIG. 3C shows the handle and cap engaged, e.g., the cap coupling portion (118) and the handle coupling portion (185) locked in place after the handle has been pushed on to the cap. The protrusions (194) of the handle coupling portion (185) snugly contain the ring (111) of the cap coupling portion (118) to lock the cap in place and contain the RBS (101) inside. In FIG. 3C, the system is ready for use.

In certain embodiments, the handle coupling portion (185) further comprises a placement guide (196) disposed on the bottom surface (192), e.g., in the snap cavity (193). The placement guide (196) may be rigid, soft, flexible, spring-like or a combination thereof (e.g., a portion of the placement guide (196) may be rigid and a portion may be soft and/or flexible). Non-limiting examples of placement guides include a metallic material, a plastic material, a ceramic material, a sponge or foam-like material, a textile material, or a combination thereof. Non-limiting examples of a placement guide includes a compression spring, a spring clip, a lever arm, a compressive foam, etc. The placement guide (196) may function to ensure the RBS is positioned in the appropriate position, e.g., the position of the RBS that ensures the prescribed or expected radiation dose is delivered to the target. For example, the placement guide (196) may function to press the RBS to the bottom surface of the cap, e.g., to the window of the cap. In certain embodiments, the placement guide (196) helps hold the RBS in place when the cap and handle are engaged, e.g., immobilize the RBS, limit the motion of the RBS, etc.

Figure 4A:
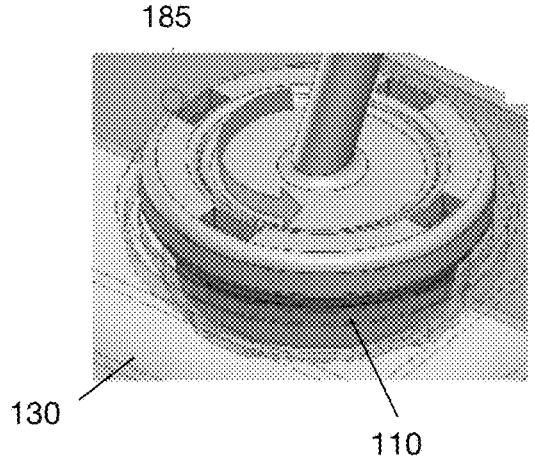
FIG. 4A shows an in-use view of System A.
Figure 4B:
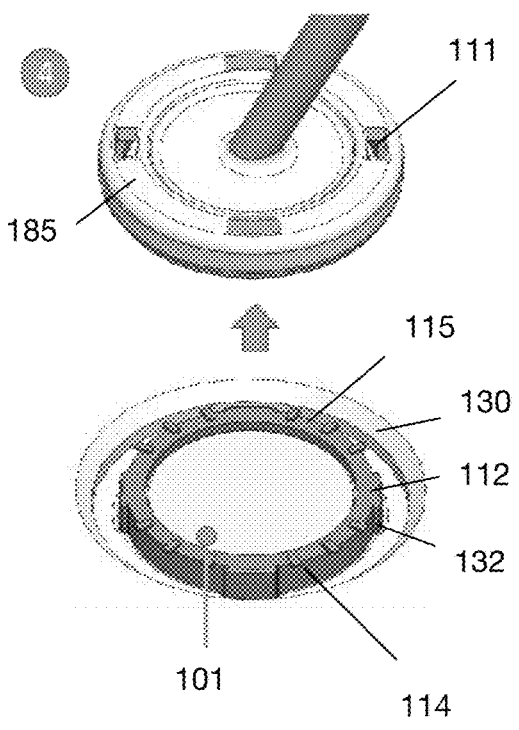
FIG. 4B shows an in-use view of System A.
Figure 4C:
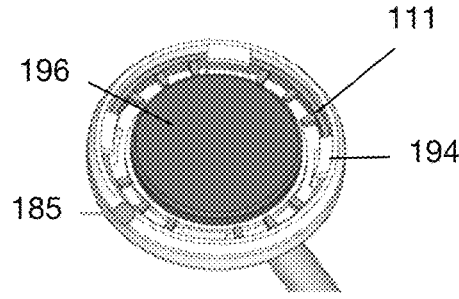
FIG. 4C shows a bottom view of the handle engagement component of System A.

FIG. 4A, FIG. 4B, and FIG. 4C show the system (100) being disassembled. In certain embodiments, the system includes a tray (130) or other item that can serve to immobilize the cap (110) during disassembly (or assembly prior to use). The cap (110) is inserted into a cavity in the tray (130). In certain embodiments, the cavity in the tray features slots (132) that are adapted to accept tabs (112) extending from the side wall of the cap (110), as shown in FIG. 4B. The tabs (112) help immobilize the cap (110), e.g., prevent the cap (110) from rotating clockwise or counterclockwise, when in the cavity of the tray (130). In certain embodiments, the tabs (112) are at a position that would clear the height of the eyelid or speculum or other particular tissue when the system is used in contact with a patient's eye, e.g., near the top edge of the cap (110). The present invention is not limited to the tabs (112) being positioned such that they would clear the eyelid or speculum, e.g., at or near the top edge of the cap (110).

When the cap (110) is inserted into the slot of the tray (130) and aligned appropriately, the handle (180) is twisted in one direction or the other. The twisting motion shears the attachment ribs (119) of the cap coupling portion (118), thereby allowing the handle (180) to be removed from the cap (110) as shown in FIG. 4B. With the ring (111) still engaged in the handle coupling portion (185) (as shown in FIG. 4C) and the attachment ribs (119) broken, the user can access the RBS (101) in the cavity of the cap (110). These alterations to the cap coupling portion and handle coupling portion render the system useless, e.g., the system cannot be re-used in the same manner (e.g., the system does not allow re-engagement of the handle and cap in the same manner), unless the system is repaired.

System B

Figures 5A, 5B, 5C:
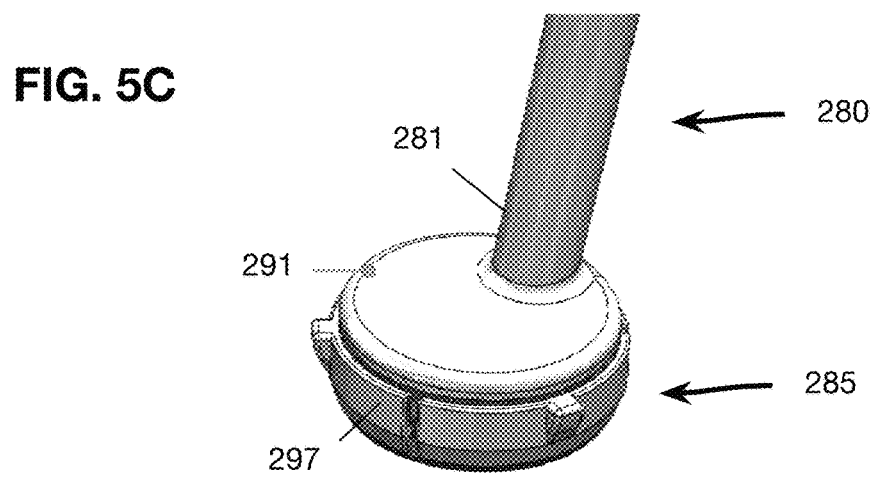
FIG. 5A shows a detailed view of the cap of System B.
FIG. 5B shows a detailed view of the handle of System B.
FIG. 5C shows a detailed view of the cap engaged with the handle of System B.

Referring to FIG. 5A and FIG. 5B, System B (200) features a cap (210) with an internal cavity (216) for temporarily housing an RBS (101). The cap may be disc-shaped (circular if viewed from the bottom or top) as shown; however, the cap (210) is not limited to any particular shape and may be rounded, oval, etc. The cap (210) has a bottom surface (213) and a side wall (214). The top of the cap (210) (opposite the bottom surface (213) is open at least partially so as to allow insertion of the RBS (101) into the internal cavity (216). The bottom surface (213) may comprise a window (213a); however, the bottom surface (213) does not necessarily comprise a window (213a).

Disposed on the outer surface (215) of the side wall (214) of the cap (110) is a cap coupling portion (218). The cap coupling portion (218) is for engaging the handle (280) as is described herein. A non-limiting example of a cap coupling portion is shown in FIG. 5A. The cap coupling portion (218) comprises one or more protrusions extending outwardly from the outer surface (215) of the side wall (214). As shown in FIG. 5A, the protrusion encircles the outer surface (215) of the side wall (214). The configuration and number of the protrusions are not limited to what is shown in FIG. 5A.

In certain embodiments, the protrusions are at a position that would clear the height of the eyelid or speculum or other particular tissue when the system is used in contact with a patient's eye, e.g., near the top edge of the cap (210). The present invention is not limited to the protrusions being positioned such that they would clear the eyelid or speculum, e.g., at or near the top edge of the cap (210).

Referring to FIG. 5B, the system (200) further comprises a handle (280) having a distal end (281) to which a handle coupling portion (285) is disposed. The handle coupling portion (285) engages the cap coupling portion (218) of the cap (210). Once the cap coupling portion (218) and the handle coupling portion (285) engage and click together or lock together, the coupling portions (218, 285) cannot be disengaged without alteration of one or both of the coupling portions (218, 285). FIG. 5C shows the handle coupling portion (285) of the handle (280) engaged with the cap (210), e.g., the cap (210) is inserted into the snap cavity (293) of the handle coupling portion (285). The handle coupling portion (285) has a top surface (291), a bottom surface (292) underneath, and a side wall (297), which forms the snap cavity (293) with the bottom surface (292).

The handle (280), e.g., the distal portion (281) of the handle, is attached to the handle coupling portion (285) at an angle, e.g., an angle formed by (i) the line of the handle (280) and (ii) the plane of the handle coupling portion (285), e.g., the plane of the top surface (291) of the handle coupling portion (285). As shown in FIG. 5B, the angle may be less than 90 degrees. In certain embodiments, the handle (280) is perpendicularly attached to the handle coupling portion (285), e.g., the angle is 90 degrees. In certain embodiments, the angle is from 10 to 20 degrees. In certain embodiments, the angle is from 20 to 30 degrees. In certain embodiments, the angle is from 30 to 40 degrees. In certain embodiments, the angle is from 40 to 50 degrees. In certain embodiments, the angle is from 50 to 60 degrees. In certain embodiments, the angle is from 60 to 70 degrees. In certain embodiments, the angle is from 70 to 80 degrees. In certain embodiments, the angle is from 80 to 90 degrees. In certain embodiments, the angle is from 45 to 90 degrees. In certain embodiments, the angle is from 60 to 90 degrees.

Figures 6A, 6B, 6C:
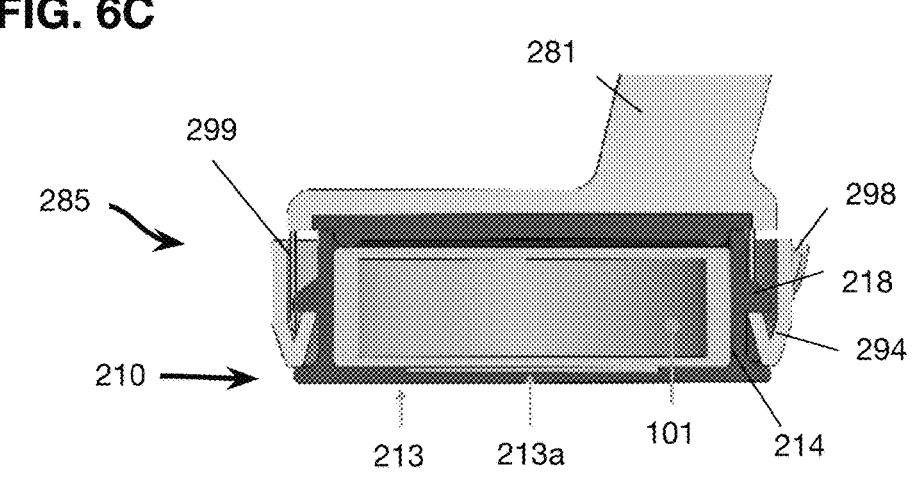
FIG. 6A shows a cross sectional view of the handle and cap of System B.
FIG. 6B shows a bottom view of the handle engagement component of System B.
FIG. 6C shows a cross sectional view of the handle and cap of System B.

FIG. 6A shows a cross sectional view of the handle coupling portion (285) of the handle (280) and the cap (210). The handle coupling portion (285) has a top surface (291) and a bottom surface (292). The handle coupling portion (285) features a side wall (297) attached to the bottom surface (292) of the handle coupling portion (285) via connecting ribs (299). The connecting ribs (299) may be spaced a distance apart, as shown in FIG. 6A; however, the present invention is not limited to this configuration. Disposed on the bottom edge of the side wall (297) and extending inwardly into the snap cavity (293) are one or more protrusions (294) that are adapted to engage the protrusions of the cap coupling portion (218).

FIG. 6C shows the handle and cap engaged, e.g., the cap coupling portion (218) and the handle coupling portion (285) locked in place after the handle has been pushed on to the cap. The protrusions (294) of the handle coupling portion (285) snugly contain the protrusions of the cap coupling portion (218) to lock the cap in place and contain the RBS (101) inside. In FIG. 6C, the system is ready for use.

In certain embodiments, the handle coupling portion (285) further comprises a placement guide (296) disposed on the bottom surface (292), e.g., in the snap cavity (293). The placement guide (296) may be rigid, soft, flexible, spring-like or a combination thereof (e.g., a portion of the placement guide (296) may be rigid and a portion may be soft and/or flexible). Non-limiting examples of placement guides include a metallic material, a plastic material, a ceramic material, a sponge or foam-like material, a textile material, or a combination thereof. Non-limiting examples of a placement guide include a compression spring, a spring clip, a lever arm, a compressive foam, etc. The placement guide (296) may function to ensure the RBS is positioned in the appropriate position, e.g., the position of the RBS that ensures the prescribed or expected radiation dose is delivered to the target. For example, the placement guide (296) may function to press the RBS to the bottom surface of the cap, e.g., to the window of the cap. In certain embodiments, the placement guide (296) helps hold the RBS in place when the cap and handle are engaged, e.g., immobilize the RBS, limit the motion of the RBS, etc.

FIG. 7A, FIG. 7B, and FIG. 7C show the system (200) being disassembled. In certain embodiments, the system includes a tray (230) or other item that can serve to immobilize the cap (210) and handle coupling portion (285) during disassembly (or assembly prior to use). The cap (210) and handle coupling portion (285) are inserted into a cavity in the tray (230). In certain embodiments, the cavity in the tray features slots (232) that are adapted to accept the tabs (298) extending from the side wall (297) of the handle coupling portion (285), as shown in FIG. 7B. The tabs (298) and the slots (232) help immobilize the cap (210) and handle coupling portion (285), e.g., prevent the cap (210) and handle coupling portion (285) from rotating clockwise or counterclockwise, when in the cavity of the tray (230).

When the cap (210) and handle coupling portion (285) are inserted into the slot of the tray (230) and aligned appropriately, the handle (280) is twisted in one direction or the other. The twisting motion shears the connecting ribs (299) of the handle coupling portion (285), thereby allowing the handle (280) to be removed from the cap (210) and handle coupling portion (285) as shown in FIG. 7B. With the side wall (297) of the handle coupling portion (285) still engaged in the cap coupling portion (285) (as shown in FIG. 7C) and the connecting ribs (299) broken, the user can access the RBS (101) in the cavity of the cap (210). These alterations to the cap coupling portion and handle coupling portion render the system useless, e.g., the system cannot be re-used in the same manner (e.g., the system does not allow re-engagement of the handle and cap in the same manner), unless the system is repaired).

System C

Referring to FIG. 8A and FIG. 8B, System C (300) features a cap (310) with an internal cavity (316) for temporarily housing an RBS (101). The cap may be disc-shaped (circular if viewed from the bottom) as shown; however, the cap (310) is not limited to any particular shape and may be rounded, oval, etc. The cap (310) has a bottom surface (313) and a side wall (314). The top of the cap (opposite the bottom surface (313) is open at least partially so as to allow insertion of the RBS (101) into the internal cavity (316). The bottom surface (313) may comprise a window (313a); however, the bottom surface (313) does not necessarily comprise a window (313a).

Disposed on the top edge (315) of the side wall (314) of the cap (310) is a cap coupling portion (118). The cap coupling portion (318) is for engaging the handle (380) as is described herein. A non-limiting example of a cap coupling portion is shown in FIG. 8A. The cap coupling portion (318) comprises a ring (311) and a plurality of attachment ribs (319) that attach the ring (311) to the top surface (315) of the side wall (314) of the cap (310). The attachment ribs (319) are spaced apart, and are not limited to the configuration shown in FIG. 8A.

In certain embodiments, the cap (310) comprises alignment tabs (312a) extending from the side wall (314) of the cap (310) and engagement tabs (312b) extending from the ring (311) of the cap coupling portion (385). The engagement tabs (312b) feature a slot for engaging the protrusions (394) of the handle coupling portion (385) as described below. In certain embodiments, one or both of the sets of tabs (312a, 312b) are at a position that would clear the height of the eyelid or speculum or other particular tissue when the system is used in contact with a patient's eye. The present invention is not limited to one or both of the sets of tabs (312a, 312b) being positioned such that they would clear the eyelid or speculum, e.g., at or near the top edge of the cap (310).

Referring to FIG. 8B, the system (300) further comprises a handle (380) having a distal end (381) to which a handle coupling portion (385) is disposed. The handle coupling portion (385) engages the cap (310), e.g., the cap coupling portion (318) of the cap (310). Once the cap coupling portion (318) and the handle coupling portion (385) engage and click together or lock together, the coupling portions (318, 385) cannot be disengaged without alteration of one or both of the coupling portions (318, 385). FIG. 8C shows the handle coupling portion (385) of the handle (380) engaged with the cap coupling portion (318) to the cap (310). FIG. 8C also shows protrusions (394) disposed on the handle coupling portion (385). The protrusions (394) engage the slot of the engagement tabs (312b) of the cap coupling portion (318) to help engage the handle coupling portion (385) and cap coupling portion (318).

The handle (380), e.g., the distal portion (381) of the handle, is attached to the handle coupling portion (385) at an angle, e.g., an angle formed by (i) the line of the handle (380) and (ii) the plane of the handle coupling portion (385), e.g., the plane of the top surface (391) of the handle coupling portion (385). As shown in FIG. 8B, the angle may be less than 90 degrees. In certain embodiments, the handle (380) is perpendicularly attached to the handle coupling portion (385), e.g., the angle is 90 degrees. In certain embodiments, the angle is from 10 to 20 degrees. In certain embodiments, the angle is from 20 to 30 degrees. In certain embodiments, the angle is from 30 to 40 degrees. In certain embodiments, the angle is from 40 to 50 degrees. In certain embodiments, the angle is from 50 to 60 degrees. In certain embodiments, the angle is from 60 to 70 degrees. In certain embodiments, the angle is from 70 to 80 degrees. In certain embodiments, the angle is from 80 to 90 degrees. In certain embodiments, the angle is from 45 to 90 degrees. In certain embodiments, the angle is from 60 to 90 degrees.

Figure 9A:
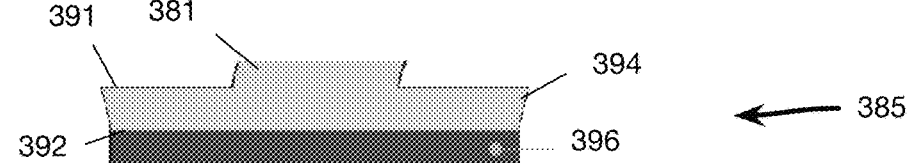
FIG. 9A shows a cross sectional view of the handle and cap of System C.
Figure 9A:
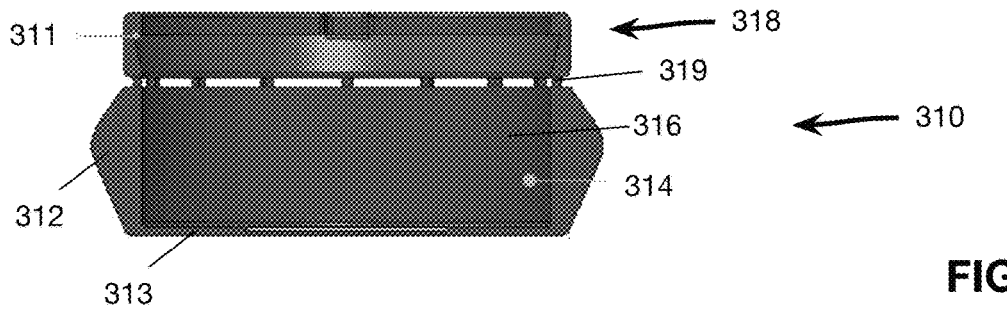
Figure 9B:
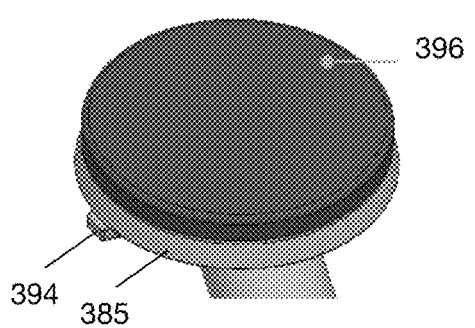
FIG. 9B shows a bottom view of the handle engagement component of System C.

FIG. 9A shows a cross sectional view of the handle coupling portion (385) of the handle (380) and the cap (310). The handle coupling portion (385) has a top surface (391) and a bottom surface (392). The protrusions (394) extend outwardly from the handle coupling portion (385).

As shown in FIG. 9A, FIG. 9B, FIG. 9C, and FIG. 9D, in certain embodiments, the handle coupling portion (385) further comprises a placement guide (396) disposed on the bottom surface (392). The placement guide (396) may be rigid, soft, flexible, spring-like or a combination thereof (e.g., a portion of the placement guide (396) may be rigid and a portion may be soft and/or flexible). Non-limiting examples of placement guides include a metallic material, a plastic material, a ceramic material, a sponge or foam-like material, a textile material, or a combination thereof. Non-limiting examples of a placement guide include a compression spring, a spring clip, a lever arm, a compressive foam, etc. The placement guide (396) may function to ensure the RBS is positioned in the appropriate position, e.g., the position of the RBS that ensures the prescribed or expected radiation dose is delivered to the target. For example, the placement guide (396) may function to press the RBS to the bottom surface of the cap, e.g., to the window of the cap. In certain embodiments, the placement guide (396) helps hold the RBS in place when the cap and handle are engaged, e.g., immobilize the RBS, limit the motion of the RBS, etc.

Figure 9C:
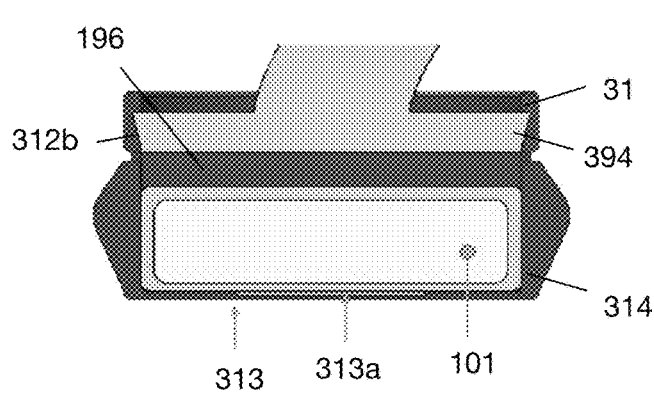
FIG. 9C shows a cross sectional view of the handle and cap of System C.
Figure 9D:
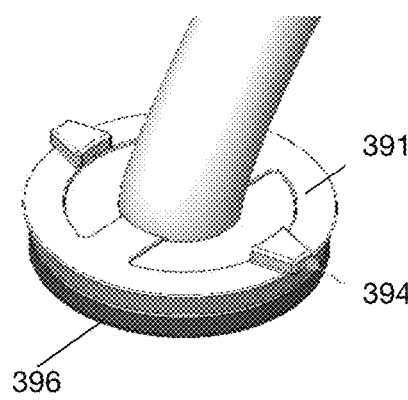
FIG. 9D shows a perspective view of System C.

FIG. 9C shows a cross-sectional view of the handle (380) and cap (310) engaged, e.g., the cap coupling portion (318) and the handle coupling portion (385) locked in place after the handle (380) has been pushed onto/into the cap (310). The protrusions (394) of the handle coupling portion (385) are engaged in the slots of the engagement tabs (312b). In FIG. 9C, the system is ready for use.

Figures 10A, 10B, 10C:
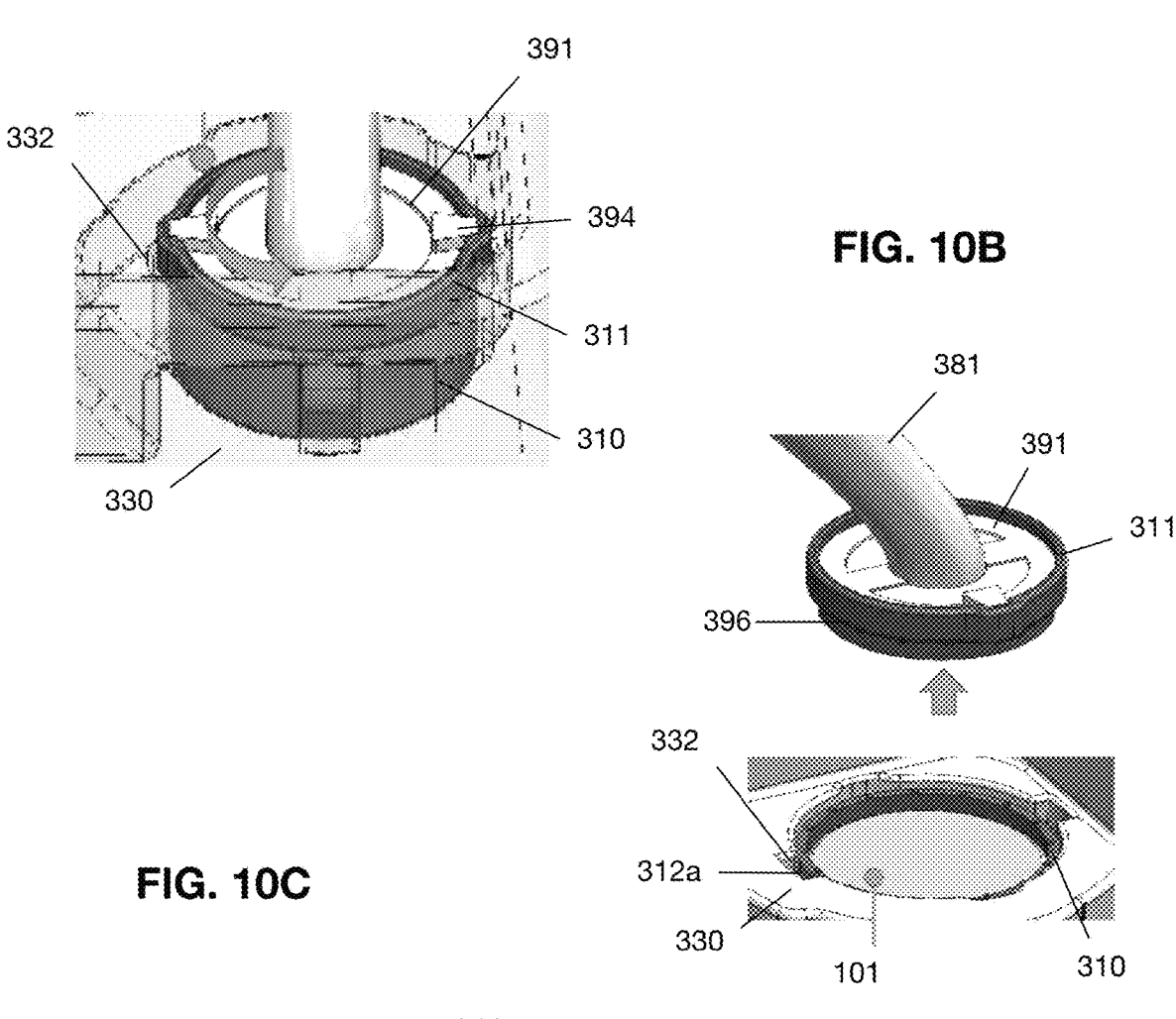
FIG. 10A shows an in-use view of System C.
FIG. 10B shows an in-use view of System C.
FIG. 10C shows a bottom view of the handle engagement component of System C.

FIG. 10A, FIG. 10B, and FIG. 10C show the system (300) being disassembled. In certain embodiments, the system includes a tray (330) or other item that can serve to immobilize the cap (310) during disassembly (or assembly prior to use). The cap (310) is inserted into a cavity in the tray (330). In certain embodiments, the cavity in the tray features slots (332) that are adapted to accept the alignment tabs (312a) extending from the side wall (314) of the cap (310), as shown in FIG. 10B. The alignment tabs (312a) and slots (332) help immobilize the cap (310), e.g., prevent the cap (310) from rotating clockwise or counterclockwise, when in the cavity of the tray (330).

When the cap (310) is inserted into the slot of the tray (330) and aligned appropriately, the handle (380) is twisted in one direction or the other. The twisting motion shears the attachment ribs (319) of the cap coupling portion (318), thereby allowing the handle (380) to be removed from the cap (310) as shown in FIG. 10B. With the ring (311) still engaged on the handle coupling portion (385) (as shown in FIG. 10B and FIG. 10C) and the attachment ribs (319) broken, the user can access the RBS (101) in the cavity of the cap (310). These alterations to the cap coupling portion and handle coupling portion render the system useless, e.g., the system cannot be re-used in the same manner (e.g., the system does not allow re-engagement of the handle and cap in the same manner), unless the system is repaired.

System D

Figure 11A:
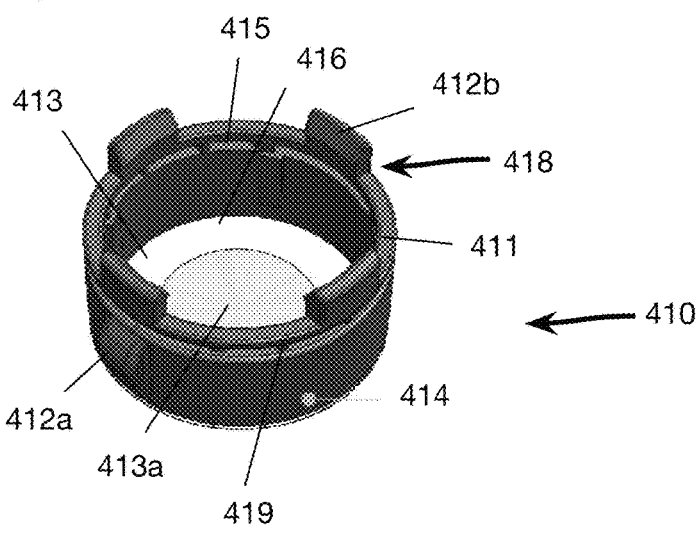
FIG. 11A shows a detailed view of the cap of System D.
Figure 11B:
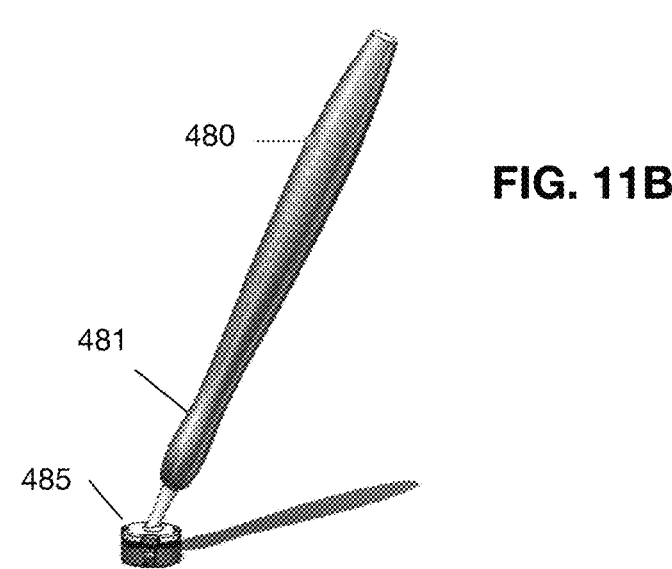
FIG. 11B shows a detailed view of the handle of System D.

Referring to FIG. 11A and FIG. 11B, System D (400) features a cap (410) with an internal cavity (416) for temporarily housing an RBS (101). The cap may be disc-shaped (circular if viewed from the bottom) as shown; however, the cap (410) is not limited to any particular shape and may be rounded, oval, etc. The cap (410) has a bottom surface (413) and a side wall (414). The top of the cap (410) (opposite the bottom surface (413) is open at least partially so as to allow insertion of the RBS (101) into the internal cavity (416). The bottom surface (413) may comprise a window (413a); however, the bottom surface (413) does not necessarily comprise a window (413a).

Disposed on the top edge (415) of the side wall (414) of the cap (410) is a cap coupling portion (418). The cap coupling portion (418) is for engaging the handle (480) as is described herein. A non-limiting example of a cap coupling portion (418) is shown in FIG. 11A. The cap coupling portion (418) comprises a ring (411) and a plurality of attachment ribs (419) that attach the ring (411) to the top surface (415) of the side wall (414) of the cap (410). The attachment ribs (419) are spaced apart, and are not limited to the configuration shown in FIG. 11A.

In certain embodiments, the cap (410) comprises alignment tabs (412a) extending from the side wall (314) of the cap (410) and engagement tabs (412b) extending upwardly from the top surface of the ring (411) of the cap coupling portion (485). In certain embodiments, the one or both sets of the tabs (412a, 412b) are at a position that would clear the height of the eyelid or speculum or other particular tissue when the system is used in contact with a patient's eye, e.g., near the top edge of the cap. The present invention is not limited to one or both sets of the tabs (412a, 412b) being positioned such that they would clear the eyelid or speculum, e.g., at or near the top edge of the cap (410).

Figure 11C:
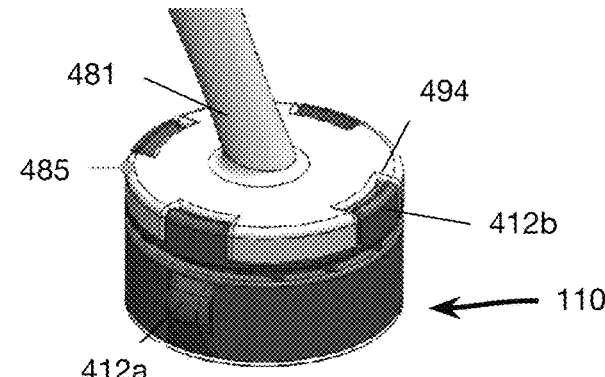
FIG. 11C shows a detailed view of the cap engaged with the handle of System D.

Referring to FIG. 11B, the system (400) further comprises a handle (480) having a distal end (481) to which a handle coupling portion (485) is disposed. The handle coupling portion (485) engages the cap (410), e.g., the cap coupling portion (418) of the cap (410). Once the cap coupling portion (418) and the handle coupling portion (485) engage and click together or lock together, the coupling portions (418, 485) cannot be disengaged without alteration of one or both of the coupling portions (418, 485). FIG. 11C shows the handle coupling portion (485) of the handle (480) engaged with the cap coupling portion (418) to the cap (410). FIG. 11C also shows indentations (494) disposed in the handle coupling portion (485). The indentations (494) engage the engagement tabs (412b) of the cap coupling portion (418) to help connect the handle coupling portion (485) and cap coupling portion (418). In certain embodiments, the indentations (494) are snaps that can snap into the cap coupling portion (418).

The handle (480), e.g., the distal portion (481) of the handle, is attached to the handle coupling portion (485) at an angle, e.g., an angle formed by (i) the line of the handle (480) and (ii) the plane of the handle coupling portion (485), e.g., the plane of the top surface (491) of the handle coupling portion (485). As shown in FIG. 11B, the angle may be less than 90 degrees. In certain embodiments, the handle (480) is perpendicularly attached to the handle coupling portion (485), e.g., the angle is 90 degrees. In certain embodiments, the angle is from 10 to 20 degrees. In certain embodiments, the angle is from 20 to 30 degrees. In certain embodiments, the angle is from 30 to 40 degrees. In certain embodiments, the angle is from 40 to 50 degrees. In certain embodiments, the angle is from 50 to 60 degrees. In certain embodiments, the angle is from 60 to 70 degrees. In certain embodiments, the angle is from 70 to 80 degrees. In certain embodiments, the angle is from 80 to 90 degrees. In certain embodiments, the angle is from 45 to 90 degrees. In certain embodiments, the angle is from 60 to 90 degrees.

Figure 12A:
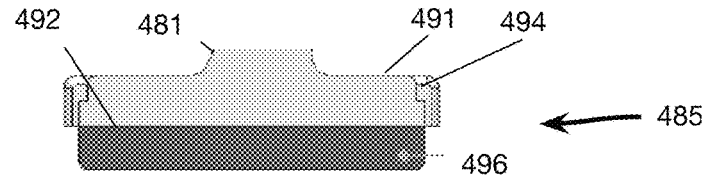
FIG. 12A shows a cross sectional view of the handle and cap of System D.
Figure 12A:
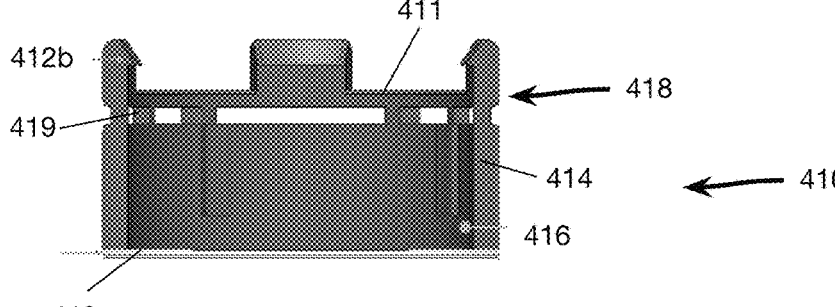
Figure 12B:
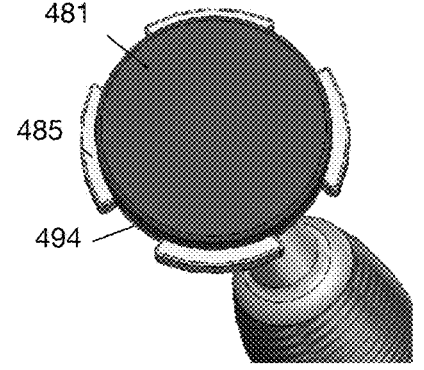
FIG. 12B shows a bottom view of the handle engagement component of System D.

FIG. 12A shows a cross sectional view of the handle coupling portion (485) of the handle (480) and the cap (410). The handle coupling portion (485) has a top surface (491) and a bottom surface (492). The indentations (494) extend inwardly into the handle coupling portion (485) (e.g., the side wall of the handle coupling portion (485)).

As shown in FIG. 12A, FIG. 12B, FIG. 12C, and FIG. 12D, in certain embodiments, the handle coupling portion (485) further comprises a placement guide (496) disposed on the bottom surface (492). The placement guide (496) may be rigid, soft, flexible, spring-like or a combination thereof (e.g., a portion of the placement guide (496) may be rigid and a portion may be soft and/or flexible). Non-limiting examples of placement guides include a metallic material, a plastic material, a ceramic material, a sponge or foam-like material, a textile material, or a combination thereof. Non-limiting examples of a placement guide include a compression spring, a spring clip, a lever arm, a compressive foam, etc. The placement guide (496) may function to ensure the RBS is positioned in the appropriate position, e.g., the position of the RBS that ensures the prescribed or expected radiation dose is delivered to the target. For example, the placement guide (496) may function to press the RBS to the bottom surface of the cap, e.g., to the window of the cap. In certain embodiments, the placement guide (496) helps hold the RBS in place when the cap and handle are engaged, e.g., immobilize the RBS, limit the motion of the RBS, etc.

Figure 12C:
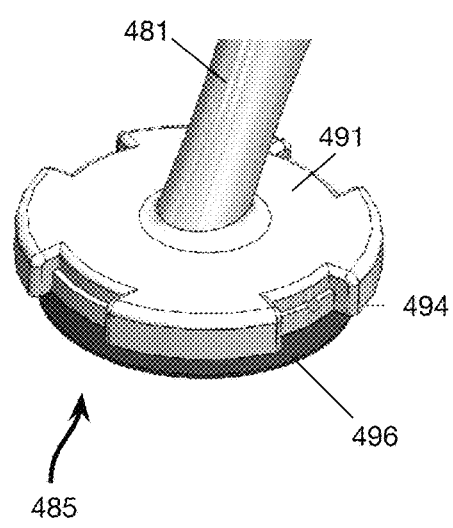
FIG. 12C shows a perspective view of the handle and cap of System D.
Figure 12D:
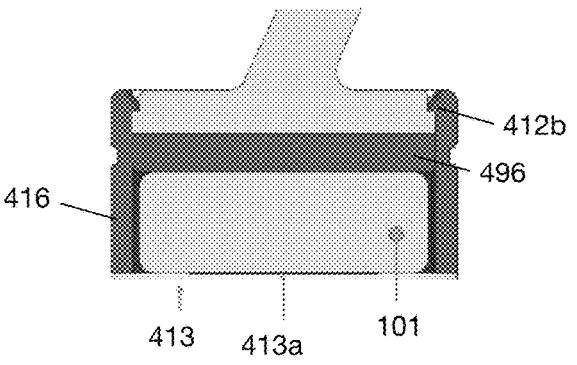
FIG. 12D shows a cross sectional view of System D.

FIG. 12D shows a cross-sectional view of the handle coupling portion (485) and cap (410) engaged, e.g., the cap coupling portion (418) and the handle coupling portion (485) locked in place after the handle (480) has been pushed onto/into the cap (410). The engagement tabs (412b) of the cap (110) snap onto the indentations (494) of the handle coupling portion (485). In FIG. 12C, the system is ready for use.

FIG. 13A, FIG. 13B, and FIG. 13C show the system (400) being disassembled. In certain embodiments, the system includes a tray (430) or other item that can serve to immobilize the cap (410) during disassembly (or assembly prior to use). The cap (410) is inserted into a cavity in the tray (430). In certain embodiments, the cavity in the tray features slots (432) that are adapted to accept the alignment tabs (412a) extending from the side wall (414) of the cap (410), as shown in FIG. 13B. The alignment tabs (412a) and slots (432) help immobilize the cap (410), e.g., prevent the cap (410) from rotating clockwise or counterclockwise, when in the cavity of the tray (430).

When the cap (410) is inserted into the slot of the tray (430) and aligned appropriately, the handle (480) is twisted in one direction or the other. The twisting motion shears the attachment ribs (419) of the cap coupling portion (418), thereby allowing the handle (480) to be removed from the cap (410) as shown in FIG. 13B. With the ring (411) still engaged on the handle coupling portion (485) (as shown in FIG. 13B and FIG. 13C) and the attachment ribs (419) broken, the user can access the RBS (101) in the cavity of the cap (410). These alterations to the cap coupling portion and handle coupling portion render the system useless, e.g., the system cannot be re-used in the same manner (e.g., the system does not allow re-engagement of the handle and cap in the same manner), unless the system is repaired).

The systems herein may be constructed from a variety of materials. For example, in certain embodiments, one or more components of the system is constructed from a material comprising polypropylene. In certain embodiments, one or more components of the system are constructed from thermoplastic elastomers. The systems of the present invention are not limited to the materials described herein.

The systems herein, or portions thereof, may be constructed from materials that can be sterilized using radiation sterilization techniques and/or gamma sterilization techniques. In certain embodiments, the systems herein, or portions thereof, may be constructed from materials that can be sterilized using standard methods such as but not limited to ethylene oxide sterilization techniques, heat (e.g., steam) sterilization techniques, vaporized hydrogen peroxide sterilization techniques, etc.

System E

Figure 14:
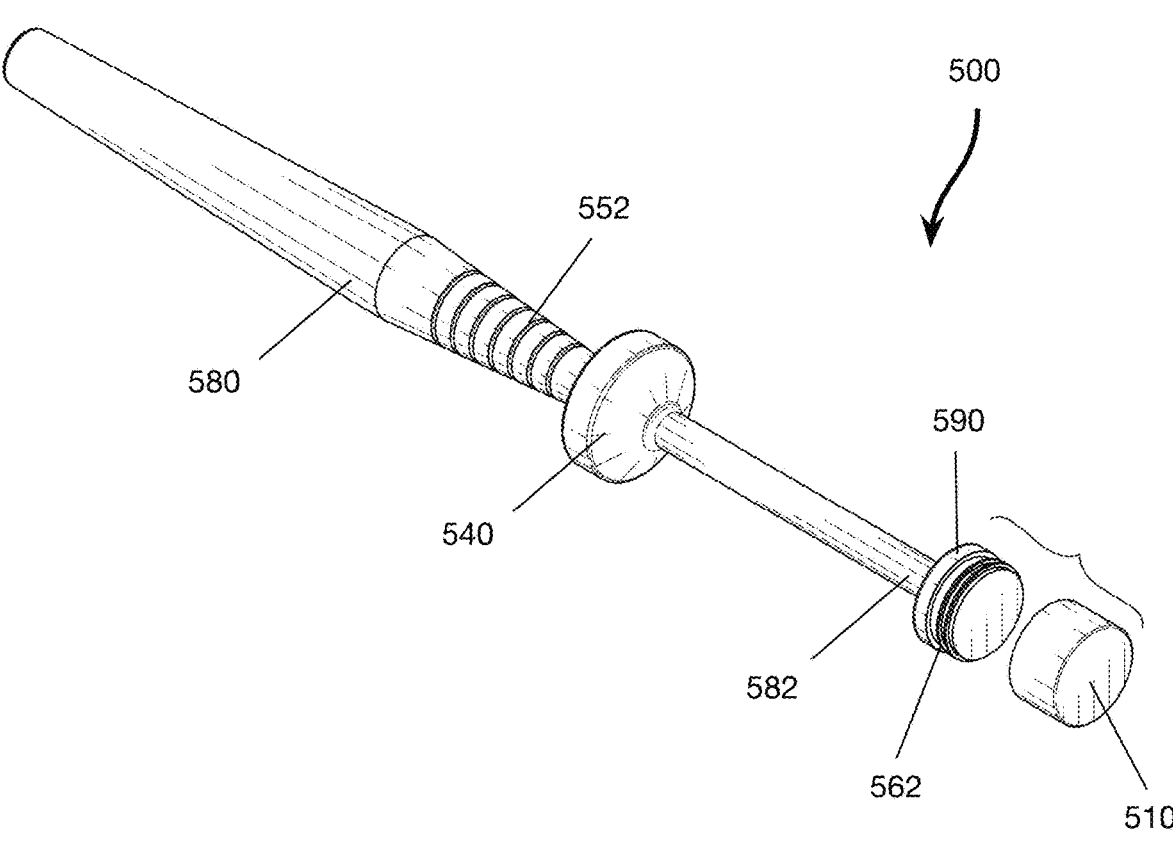
FIG. 14 shows a perspective view of an embodiment of the present invention.

Referring to FIG. 14, System E (500) features a handle (580) having a distal end (582) that engages a cap (510) with an internal cavity for temporarily housing an RBS. For example, an RBS may be inserted into the internal cavity of the cap (510), and the handle (580) may be temporarily attached to or connected to the handle (580).

As shown, the cap (510) features threads that threadably engage complementary threads (562) disposed on the distal end (582) of the handle (580). In certain embodiments, a handle head (590) is disposed at the distal end (582) of the handle (580), and the complementary threads (562 are disposed on the handle head (590) as shown in FIG. 14.

In certain embodiments, the handle is not uniform in diameter, e.g., certain portions may have a larger diameter than others. As shown in FIG. 14, the diameter of the handle narrows where the user's fingers grip the handle, as compared to portions of the handle that are more proximal. In certain embodiments, a grip (552) is disposed on the handle. The grip is not limited to any particular configuration, as grips are well known to one of ordinary skill in the art.

Referring to FIG. 14, in some embodiments, the system features a shield (540) disposed on the handle and extending outwardly from the handle. The shield (540) may function to help the user's hand maintain a grip on the appropriate portion of the handle, e.g., help prevent the user's fingers from sliding towards the distal end of the handle. This can help the user maintain the appropriate grip on the handle as well as avoid unnecessary exposure to additional radiation if his/her fingers were too close to the distal end. In some embodiments, the shield (540) may function to block a portion of the radiation that extends backwardly toward the user's fingers.

System F

Figure 15:
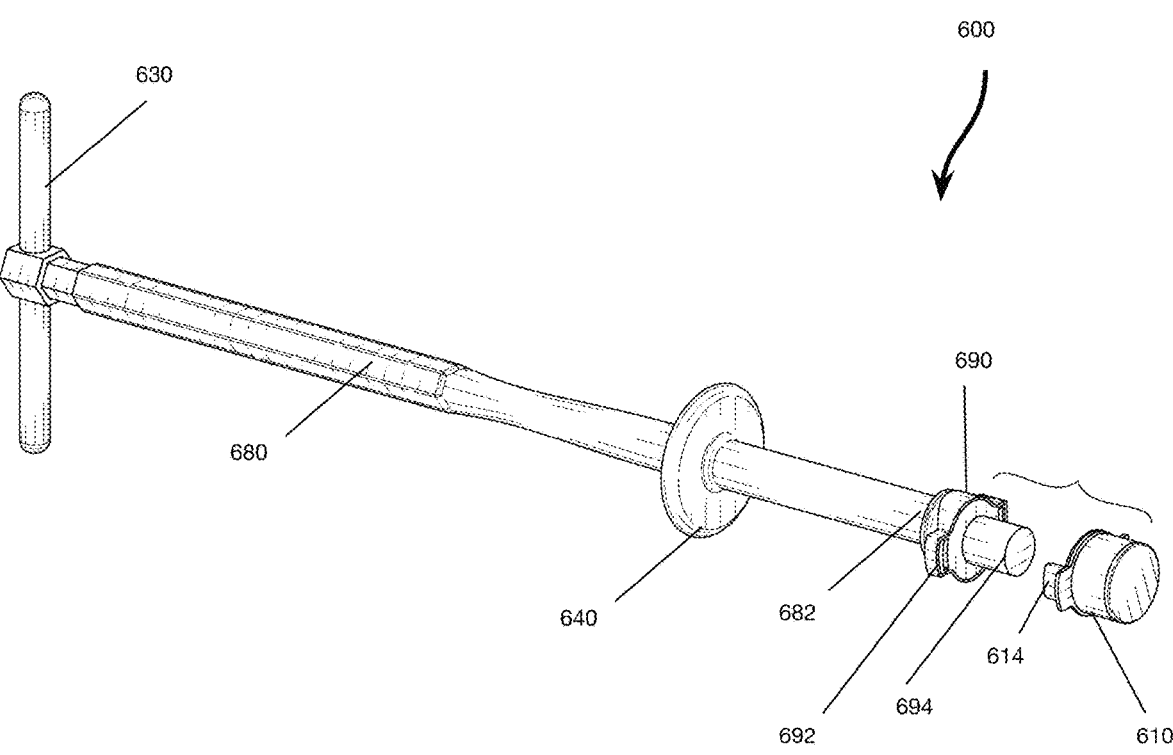
FIG. 15 shows a perspective view of an embodiment of the present invention.

Referring to FIG. 15, System E (600) features a handle (680) having a distal end (682) that engages a cap (610) with an internal cavity for temporarily housing an RBS. For example, an RBS may be inserted into the internal cavity of the cap (610), and the handle (680) may be temporarily attached to or connected to the handle (680).

As shown, in some embodiments, the cap (610) features tabs (614) that protrude upwardly, e.g., in the direction of the handle (e.g., when the handle is attached to the cap (610)). The handle (680) may feature a handle head (690) disposed at the distal end (682) of the handle (680), and the handle head (690) may feature a tab lock (692) that engages the tabs (614) of the cap (610) to secure the cap (610) to the handle (680), e.g., temporarily. In some embodiments, the system features a pair of opposing tabs (614) and tab locks (692).

In some embodiments, the handle head (690) further comprises a stabilizer (694), e.g., an extension of the handle head (690) that extends into the inner cavity of the cap (610) to help stabilize the RBS therein, e.g., to prevent it from moving in the x, y, or z direction.

In certain embodiments, the handle is not uniform in diameter, e.g., certain portions may have a larger diameter than others. For example, the diameter of the handle may narrow where the user's fingers grip the handle, as compared to portions of the handle that are more proximal.

As shown in FIG. 15, the proximal end (581) of the handle (580) may feature a grip (630) that may be used to help attach the cap to the handle or rotate the handle with respect to the cap, e.g., during disassembly. The grip (630) is not limited to the configuration shown in FIG. 15.

Referring to FIG. 15, in some embodiments, the system features a shield (640) disposed on the handle and extending outwardly from the handle. The shield (640) may function to help the user's hand maintain a grip on the appropriate portion of the handle, e.g., help prevent the user's fingers from sliding towards the distal end of the handle. This can help the user maintain the appropriate grip on the handle as well as avoid unnecessary exposure to additional radiation if his/her fingers were too close to the distal end. In some embodiments, the shield (640) may function to block a portion of the radiation that extends backwardly toward user's fingers.

EXAMPLE A

The following is a non-limiting example of methods of the present invention using System A, e.g., as shown in FIG. 2A, FIG. 2B, FIG. 2C, FIG. 3A, FIG. 3B, FIG. 3C, FIG. 4A, FIG. 4B, and FIG. 4C. It is to be understood that said example is not intended to limit the present invention in any way. Equivalents or substitutes are within the scope of the present invention.

The system (100) may be packaged in a tray or other packaging unit. Upon opening the tray or package, the handle (180) may be removed and the RBS (101) can be inserted into the cap (110). After removing the handle (180) from the tray or package, the handle (180) is pushed down on top of the cap (110) until snapping occurs. This secures the RBS (101) within the cap (110). For example, the protrusions (194) of the handle coupling portion (185) snugly contain the ring (111) of the cap coupling portion (118) to lock the cap in place and contain the RBS (101) inside.

The system (100) may be used, e.g., the cap may be placed in contact with a target tissue such as eye tissue to provide radiation to the target.

After use, the cap (110) is separated from the handle (180) to expose the RBS (101) for removal. In certain embodiments, the cap (110) is placed into a cavity in the tray (130). The cavity in the tray (130) may feature slots (132) that accept tabs (112) on the cap (110) so as to orient the cap (110) during insertion and immobilize the cap (110) during the process of removing the handle (180). For example, in certain embodiments, the tabs (112) help prevent the cap (110) from rotating clockwise or counterclockwise, when in the cavity of the tray (130).

When the cap (110) is inserted into the slot of the tray (130) and aligned appropriately, the handle (180) is twisted in one direction or the other. The twisting motion shears the attachment ribs (119) of the cap coupling portion (118), thereby allowing the handle (180) to be removed from the cap (110). The ring (111) remains engaged in with the handle coupling portion (185) and the attachment ribs (119) are broken. Thus, the user can access the RBS (101) in the cavity of the cap (110), and the system is rendered useless, e.g., the system cannot be re-used in the same manner (e.g., the system does not allow re-engagement of the handle and cap in the same manner), unless the system is repaired).

EXAMPLE B

The following is a non-limiting example of an example of methods of the present invention using System B, e.g., as shown in FIG. 5A, FIG. 5B, FIG. 5C, FIG. 6A, FIG. 6B, FIG. 6C, FIG. 7A, FIG. 7B, and FIG. 7C. It is to be understood that said example is not intended to limit the present invention in any way. Equivalents or substitutes are within the scope of the present invention.

The system (200) may be packaged in a tray or other packaging unit. Upon opening the tray or package, the handle (280) may be removed and the RBS (101) can be inserted into the cap (210). After removing the handle (180) from the tray or package, the handle (280) is pushed down on top of the cap (210) until snapping occurs. This secures the RBS (101) within the cap (210). For example, the protrusions (294) of the handle coupling portion (285) snugly contain the protrusions of the cap coupling portion (218) to lock the cap in place and contain the RBS (101) inside.

The system (200) may be used, e.g., the cap may be placed in contact with a target tissue such as eye tissue to provide radiation to the target.

After use, the cap (210) and the handle coupling portion (285) are separated from the handle (280) to expose the RBS (101) for removal. In certain embodiments, the cap (210) and handle coupling portion (285) are placed into a cavity in the tray (230). The cavity in the tray (230) may feature slots (232) that accept tabs (298) on the handle coupling portion (285) so as to orient the handle coupling portion (285) during insertion and immobilize the handle coupling portion (285) during the process of removing the handle (280) from the handle coupling portion (285). For example, in certain embodiments, the tabs (298) help prevent the handle coupling portion (285) from rotating clockwise or counterclockwise, when in the cavity of the tray (230).

When the cap (210) and handle coupling portion (285) are inserted into the slot of the tray (130) and aligned appropriately, the handle (180) is twisted in one direction or the other. The twisting motion shears the connecting ribs (299) of the handle coupling portion (285), thereby allowing the handle (180) to be removed from the handle coupling portion (285). With the side wall (297) of the handle coupling portion (285) still engaged in the cap coupling portion (285) and the connecting ribs (299) broken, the user can access the RBS (101) in the cavity of the cap (210), and the system is rendered useless, e.g., the system cannot be re-used in the same manner (e.g., the system does not allow re-engagement of the handle and cap in the same manner), unless the system is repaired).

EXAMPLE C

The following is a non-limiting example of an example of methods of the present invention using System C, e.g., as shown in FIG. 8A, FIG. 8B, FIG. 8C, FIG. 9A, FIG. 9B, FIG. 9C, FIG. 9D, FIG. 10A, FIG. 10B, and FIG. 10C. It is to be understood that said example is not intended to limit the present invention in any way. Equivalents or substitutes are within the scope of the present invention.

The system (300) may be packaged in a tray or other packaging unit. Upon opening the tray or package, the handle (380) may be removed and the RBS (101) can be inserted into the cap (310). After removing the handle (380) from the tray or package, the handle (380) is pushed down into the cap (310) until snapping occurs. The protrusions (394) of the handle coupling portion (385) engage the slots of the engagement tabs (312b). This secures the RBS (101) within the cap (310).

The system (300) may be used, e.g., the cap may be placed in contact with a target tissue such as eye tissue to provide radiation to the target.

After use, the cap (310) and the handle coupling portion (385) are separated from the handle (380) to expose the RBS (101) for removal. In certain embodiments, the cap (310) and handle coupling portion (385) are placed into a cavity in the tray (330). The cavity in the tray (330) may feature slots (332) that accept the alignment tabs (312a) on the cap (310) so as to orient the cap (310) during insertion and immobilize the cap (310) during the process of removing the handle (380) from cap (310). For example, in certain embodiments, the alignment tabs (312a) help prevent the cap (310) from rotating clockwise or counterclockwise when in the cavity of the tray (330).

When the cap (310) is inserted into the slot of the tray (330) and aligned appropriately, the handle (380) is twisted in one direction or the other. The twisting motion shears the attachment ribs (319) of the cap coupling portion (318), thereby allowing the handle (380) to be removed from the cap (310). With the ring (311) still engaged on the handle coupling portion (385) and the attachment ribs (319) broken, the user can access the RBS (101) in the cavity of the cap (310), and the system is rendered useless, e.g., the system cannot be re-used in the same manner (e.g., the system does not allow re-engagement of the handle and cap in the same manner), unless the system is repaired).

EXAMPLE D

The following is a non-limiting example of an example of methods of the present invention using System D, e.g., as shown in FIG. 11A, FIG. 11B, FIG. 11C, FIG. 12A, FIG. 12B, FIG. 12C, FIG. 12D, FIG. 13A, FIG. 13B, and FIG. 13C. It is to be understood that said example is not intended to limit the present invention in any way. Equivalents or substitutes are within the scope of the present invention.

The system (400) may be packaged in a tray or other packaging unit. Upon opening the tray or package, the handle (480) may be removed and the RBS (101) can be inserted into the cap (410). After removing the handle (480) from the tray or package, the handle (480) is pushed down onto the cap (410) until snapping occurs. The engagement tabs (412*b*) of the cap (410) snap onto the protrusions (494) of the handle coupling portion (485). This secures the RBS (101) within the cap (410).

The system (400) may be used, e.g., the cap may be placed in contact with a target tissue such as eye tissue to provide radiation to the target.

After use, the cap (410) and the handle coupling portion (485) are separated from the handle (480) to expose the RBS (101) for removal. In certain embodiments, the cap (410) and handle coupling portion (485) are placed into a cavity in the tray (430). The cavity in the tray (430) may feature slots (432) that accept the alignment tabs (412*a*) on the cap (410) so as to orient the cap (410) during insertion and immobilize the cap (410) during the process of removing the handle (480) from cap (410). For example, in certain embodiments, the alignment tabs (412*a*) help prevent the cap (410) from rotating clockwise or counterclockwise when in the cavity of the tray (430).

When the cap (410) is inserted into the slot of the tray (430) and aligned appropriately, the handle (480) is twisted in one direction or the other. The twisting motion shears the attachment ribs (419) of the cap coupling portion (418), thereby allowing the handle (480) to be removed from the cap (410). With the ring (411) still engaged on the handle coupling portion (485) and the attachment ribs (419) broken, the user can access the RBS (101) in the cavity of the cap (410), and the system is rendered useless, e.g., the system cannot be re-used in the same manner (e.g., the system does not allow re-engagement of the handle and cap in the same manner), unless the system is repaired).

Embodiments of the present invention can be freely combined with each other if they are not mutually exclusive.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application and are exemplary, and are not intended in any way to limit the scope of the claims to the particular features having the corresponding reference numbers in the drawings.

What is claimed is:

1. A brachytherapy system comprising:
a) a cap with an internal cavity for accepting a radionuclide brachytherapy source (RBS):
b) a handle comprising a handle coupling portion at a distal end for attaching to the cap; and
c) a cap coupling portion disposed on the cap for engaging the handle coupling portion,
wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging; and
wherein the cap coupling portion comprises a ring attached to a top surface of the cap via one or more attachment ribs, and the handle coupling portion is configured to snap onto the ring, and disengagement of the handle coupling portion and cap coupling portion results in the shearing of the attachment ribs and the ring remains snapped onto the handle coupling portion.

2. A brachytherapy system comprising:
a) a cap with an internal cavity for accepting a radionuclide brachytherapy source (RBS):
b) a handle comprising a handle coupling portion at a distal end for attaching to the cap, wherein the handle coupling portion comprises a snap cavity (193) disposed on a bottom surface (192); and
c) a cap coupling portion disposed on the cap for engaging the handle coupling portion, wherein the cap coupling portion (118) comprises a ring (111) and a plurality of attachment ribs (119) that attach the ring (110) to a top surface (115) of a side wall (114) of the cap (110);
wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging; and
wherein the handle coupling portion (185) and cap coupling portion (118) can engage to house the RBS in the internal cavity (116) as the ring (111) is configured to snap into the snap cavity (113) of the handle coupling portion (185), and disengagement of the handle coupling portion (185) and cap coupling portion (118) alters the handle coupling portion (185), the cap coupling portion (118), or both the handle coupling portion (185) and the cap coupling portion (118) such that the handle coupling portion (185) and cap coupling portion (118) cannot re-engage as was previously done.

3. A brachytherapy system comprising:
a) a cap with an internal cavity for accepting a radionuclide brachytherapy source (RBS);
b) a handle comprising a handle coupling portion at a distal end for attaching to the cap; wherein the handle coupling portion (285) comprises a snap cavity (293) for accepting the cap (210), and
c) a cap coupling portion disposed on the cap for engaging the handle coupling portion, wherein the cap coupling portion (218) comprises one or more protrusions extending outwardly from an outer surface of a side wall of the cap (210);
wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging; and
wherein the handle coupling portion (285) and cap coupling portion (218) engage to house the RBS in the internal cavity (216) as the protrusions of the cap coupling portion (218) are configured to lock inside the snap cavity (293) of the handle coupling portion (285), and disengagement of the handle coupling portion (285) and cap coupling portion (218) alters the handle coupling portion (285), the cap coupling portion (218), or both the handle coupling portion (285) and the cap coupling portion (218) such that the handle coupling portion (285) and cap coupling portion (218) cannot re-engage as was previously done.

4. A brachytherapy system (600) comprising:

a. a cap (610) with an internal cavity for accepting a radionuclide brachytherapy source (RBS);

b. a handle (680) comprising a handle coupling portion (690) at a distal end (682) for attaching to the cap (610), the handle coupling portion (690) comprises a tab lock (692); and c. a cap coupling portion disposed on the cap for engaging the handle coupling portion, the cap coupling portion comprises a tab (692) that protrudes upwardly from the cap (610) and can snap into the tab lock (692) of the handle (680);

wherein the handle coupling portion and cap coupling portion are configured to engage in a first position wherein the tab (692) is engaged with the tab lock (692) so as to house and secure the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging.

5. A brachytherapy system comprising:

a) a radionuclide brachytherapy source (RBS);

b) a cap with an internal cavity for accepting a radionuclide brachytherapy source (RBS);

c) a handle comprising a handle coupling portion at a distal end for attaching to the cap; and d) a cap coupling portion disposed on the cap for engaging the handle coupling portion;

wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging; and wherein the cap coupling portion comprises a ring attached to a top surface of the cap via one or more attachment ribs, and the handle coupling portion is configured to snap onto the ring, and disengagement of the handle coupling portion and cap coupling portion results in the shearing of the attachment ribs and the ring remains snapped onto the handle coupling portion.

6. A brachytherapy system comprising:

a) a radionuclide brachytherapy source (RBS);

b) a cap with an internal cavity for accepting a radionuclide brachytherapy source (RBS);

c) a handle comprising a handle coupling portion at a distal end for attaching to the cap, wherein the handle coupling portion comprises a snap cavity (193) disposed on a bottom surface (192); and d) a cap coupling portion disposed on the cap for engaging the handle coupling portion; wherein the cap coupling portion (118) comprises a ring (111) and a plurality of attachment ribs (119) that attach the ring (110) to a top surface (115) of a side wall (114) of the cap (110);

wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging, and wherein the handle coupling portion (185) and cap coupling portion (118) can engage to house the RBS in the internal cavity (116) as the ring (111) is configured to snap into the snap cavity (113) of the handle coupling portion (185), and disengagement of the handle coupling portion (185) and cap coupling portion (118) alters the handle coupling portion (185), the cap coupling portion (118), or both the handle coupling portion (185) and the cap coupling portion (118) such that the handle coupling portion (185) and cap coupling portion (118) cannot re-engage as was previously done.

7. A brachytherapy system comprising:

a) a radionuclide brachytherapy source (RBS);

b) a cap with an internal cavity for accepting a radionuclide brachytherapy source (RBS);

c) a handle comprising a handle coupling portion at a distal end for attaching to the cap, wherein the handle coupling portion (285) comprises a snap cavity (293) for accepting the cap (210), and d) a cap coupling portion disposed on the cap for engaging the handle coupling portion; wherein the cap coupling portion (218) comprises one or more protrusions extending outwardly from an outer surface of a side wall of the cap (210);

wherein the handle coupling portion and cap coupling portion are configured to engage in a first position so as to house the RBS in the internal cavity, and the handle coupling portion and cap coupling portion are configured to be physically altered to a second position upon disengagement of the handle coupling portion and cap coupling portion, wherein the second position prevents the handle coupling portion and the cap coupling portion from re-engaging, and wherein the handle coupling portion (285) and cap coupling portion (218) engage to house the RBS in the internal cavity (216) as the protrusions of the cap coupling portion (218) are configured to lock inside the snap cavity (293) of the handle coupling portion (285), and disengagement of the handle coupling portion (285) and cap coupling portion (218) alters the handle coupling portion (285), the cap coupling portion (218), or both the handle coupling portion (285) and the cap coupling portion (218) such that the handle coupling portion (285) and cap coupling portion (218) cannot re-engage as was previously done.

* * * * *